(12) United States Patent
Keyt et al.

(10) Patent No.: US 6,750,044 B1
(45) Date of Patent: Jun. 15, 2004

(54) VARIANTS OF VASCULAR ENDOTHELIAL CELL GROWTH FACTOR HAVING ANTAGONISTIC PROPERTIES, NUCLEIC ACIDS ENCODING THE SAME AND HOST CELLS COMPRISING THOSE NUCLEIC ACIDS

(75) Inventors: Bruce A. Keyt, Pacifica, CA (US); Francis Hung Nguyen, Daly City, CA (US); Napoleone Ferrara, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 08/734,443

(22) Filed: Oct. 17, 1996

(51) Int. Cl.[7] .................. A61K 38/19; C07K 14/52; C12N 5/10; C12N 15/19; C12N 15/63
(52) U.S. Cl. ............... 435/69.4; 435/320.1; 435/325; 435/358; 514/12; 530/399; 530/402; 536/23.5
(58) Field of Search ............... 435/69.4, 320.1, 435/325, 358; 536/23.5, 23.51; 530/399, 402; 514/12

(56) References Cited

U.S. PATENT DOCUMENTS

| | | |
|---|---|---|
| 4,456,550 A | 6/1984 | Dvorak et al. |
| 5,008,196 A | 4/1991 | Connolly et al. |
| 5,036,003 A | 7/1991 | Olander et al. |
| 5,185,438 A | 2/1993 | Lemischka |
| 5,240,848 A | 8/1993 | Keck et al. |
| 5,418,135 A * | 5/1995 | Pang .................. 435/7.1 |

FOREIGN PATENT DOCUMENTS

| | | |
|---|---|---|
| WO | 92/14748 | 9/1992 |
| WO | 92/17486 | 10/1992 |
| WO | 94/11499 | 5/1994 |
| WO | 94/21679 | 9/1994 |
| WO | 95/33050 | 12/1995 |

OTHER PUBLICATIONS

Claffey et al. Biochim. Biophys. Acta 1246: 1–9, 1995.*
Pötgens et al. J. Biol. Chem. 269(52):32879–32885, 1994.*
Ferrara, N., et al., "The Vascular Endothelial Growth Factor Family of Polypeptides", *Journal of Cellular Biochemistry*, 47:211–218(1991).
Tischer, E., et al., "The Human Gene for Vascular Endothelial Growth Factor", *The Journal of Biological Chemistry*, 266(18):11947–11954(1991).
Tischer, E., et al. "Vascular Endothelial Growth Factor: A New Membrane of The Platelet–Derived Growth Factor Gene Family", *Biochemical and Biophysical Research Communications*, 165(3):1198–1206(1989).

* cited by examiner

*Primary Examiner*—Christine J. Saoud
(74) *Attorney, Agent, or Firm*—Merchant & Gould P.C.

(57) ABSTRACT

The present invention involves the preparation of vascular endothelial growth factor (VEGF) antagonist molecules comprising variant VEGF polypeptides which are capable of binding to and occupying cell surface VEGF receptors without inducing a VEGF response, thereby antagonizing the biological activity of the native VEGF protein. Specifically, the variant VEGF polypeptides of the present invention comprise modifications of at least one cysteine residue in the native VEGF sequence, thereby inhibiting the ability of the variant polypeptide to dimerize through the formation of disulfide bonds. The present invention is further directed to methods for preparing such variant VEGF antagonists and to methods, compositions and assays utilizing such variants for producing pharmaceutically active materials having therapeutic and pharmacologic properties that differ from the native VEGF protein.

16 Claims, 9 Drawing Sheets

FIG. 1A

```
  1   CAGTGTGCTG GCGGCCCGGC GCGAGCCGGC CCGGCCCCGG TCGGGCCTCC
-26

GAAACC    ATG AAC TTT CTG CTG TCT TGG GTG CAT TGG AGC
                 M   N   F   L   L   S   W   V   H   W   S
                -26                            -20

90   CTC GCC TTG CTG CTC TAC CTC CAC CAT GCC AAG TGG TCC CAG
-15    L   A   L   L   L   Y   L   H   H   A   K   W   S   Q
                           -10

GCT|GCA CCC ATG GCA GAA GGA GGA GGG CAG AAT CAT CAC
       A | A→ P   M   A   E   G   G   G   Q   N   H   H
      -1   +1                  +5                  +10

171   GAA GTG GTG AAG TTC ATG GAT GTC TAT CAG CGC AGC TAC TGC
 13    E   V   V   K   F   M   D   V   Y   Q   R   S   Y   C
          +15                  +20                  +25 +26

CAT CCA ATC GAG ACC CTG GTG GAC ATC TTC CAG GAG TAC
       H   P   I   E   T   L   V   D   I   F   Q   E   Y
               I  +30                  +35

252   CCT GAT GAG ATC GAG TAC ATC TTC AAG CCA TCC TGT GTG CCC
 40    P   D   E   I   E   Y   I   F   K   P   S   C   V   P
      +40                  +45                  +50 +51

CTG ATG CGA TGC GGG GGC TGC TGC AAT GAC GAG GGC CTG
       L   M   R   C   G   G   C   C   N   D   E   G   L
          +55     +57         +60 +61              +65

333   GAG TGT GTG CCC ACT GAG GAG TCC AAC ATC ACC ATG CAG ATT
 67    E   C   V   P   T   E   E   S   N   I   T   M   Q   I
          +68     +70                  +75                  +80

ATG CGG ATC AAA CCT CAC CAA GGC CAG CAC ATA GGA GAG
       M   R   I   K   P   H   Q   G   Q   H   I   G   E
                      +85                  +90

414   ATG AGC TTC CTA CAG CAC AAC AAA TGT GAA TGC AGA CCA AAG
 94    M   S   F   L   Q   H   N   K   C   E   C   R   P   K
          +95                 +100    +102    +104 +105

AAA GAT AGA GCA AGA CAA GAA AAT CCC TGT GGG CCT TGC
       K   D   R   A   R   Q   E   N   P   C   G   P   C
              +110                 +115    +117         +120

495   TCA GAG CGG AGA AAG CAT TTG TTT GTA CAA GAT CCG CAG ACG
121    S   E   R   R   K   H   L   F   V   Q   D   P   Q   T
                      +125                 +130

TGT AAA TGT TCC TGC AAA AAC ACA GAC TCG CGT TGC AAG
       C   K   C   S   C   K   N   T   D   S   R   C   K
      +135    +137    +139 +140                  +145 +146
```

FIG. 1B

```
576  GCG AGG CAG CTT GAG TTA AAC GAA CGT ACT TGC AGA TGT GAC
148   A   R   Q   L   E   L   N   E   R   T   C   R   C   D
                 +150            +155        +158    +160

AAG CCG AGG CGG TGA GCCGGGCA GGAGGAAGGA GCCTCCCTCA
      K   P   R   R   O
                  +165

661  GGGTTTCGGG AACCAGATCT CTCACCAGGA AAGACTGATA CAGAACGATC

GATACAGAAA CCACGCTGCC GCCACCACAC CATCACCATC GACAGAACAG

761  TCCTTAATCC AGAAACCTGA ATGAAGGAA GAGGAGACTC TGCGCAGAGC

ACTTTGGGTC CGGAGGGCGA GACTCCGGCG GAAGCATTCC CGGGCGGGTG

861  ACCCAGCACG GTCCCTCTTG GAATTGGATT CGCCATTTTA TTTTTCTTGC

TGCTAAATCA CCGAGCCCGG AAGATTAGAG AGTTTTATTT CTGGGATTCC

961  TGTAGACACA CCGCGGCCGC CAGCACACTG
```

VARIANTS OF VASCULAR ENDOTHELIAL CELL GROWTH FACTOR HAVING ANTAGONISTIC PROPERTIES, NUCLEIC ACIDS ENCODING THE SAME AND HOST CELLS COMPRISING THOSE NUCLEIC ACIDS

FIELD OF THE INVENTION

The present invention is directed to particular variants of vascular endothelial cell growth factor (hereinafter sometimes referred to as VEGF) which bind to and occupy cell surface VEGF receptors without inducing a VEGF response, thereby antagonizing the biological activity of the native VEGF protein. The present invention is further directed to methods for preparing such variant VEGF antagonists and to methods, compositions and assays utilizing such variants for producing pharmaceutically active materials having therapeutic and pharmacologic properties that differ from the native VEGF protein.

BACKGROUND OF THE INVENTION

The two major cellular components of the mammalian vascular system are the endothelial and smooth muscle cells. Endothelial cells form the lining of the inner surface of all blood vessels in the mammal and constitute a non-thrombogenic interface between blood and tissue. Therefore, the proliferation of endothelial cells is,an important component for the development of new capillaries and blood vessels which, in turn, is a necessary process for the growth and/or regeneration of mammalian tissues. One protein that has been shown to play an extremely important role in promoting endothelial cell proliferation and angiogenesis is vascular endothelial cell growth factor (VEGF). VEGF is a heparin-binding endothelial cell-specific growth factor which was originally identified and purified from media conditioned by bovine pituitary follicular or folliculostellate (FS) cells. Ferrara and Henzel, *Biochem. Biophys. Res. Comm.* 161:851–858 (1989). Naturally-occurring VEGF is a dimeric protein having an apparent molecular mass of about 46 kDa with each subunit having an apparent molecular mass of about 23 kDa. Normal dimerization between individual native VEGF monomers occurs through the formation of disulfide bonds between the cysteine residues located at amino acid position 51 of one monomeric unit bonding to the cysteine residue at amino acid position 60 of another monomeric unit and vice versa. Human VEGF is expressed in a variety of tissues as multiple homodimeric forms (121, 165, 189 and 206 amino acids per monomer), wherein each form arises as a result of alternative splicing of a single RNA transcript. For example, $VEGF_{121}$ is a soluble mitogen that does not bind heparin whereas the longer forms of VEGF bind heparin with progressively higher affinity.

Biochemical analyses have shown that the native VEGF dimer exhibits a strong mitogenic specificity for vascular endothelial cells. For example, media conditioned by cells transfected by human VEGF cDNA promoted the proliferation of capillary endothelial cells, whereas medium conditioned by control cells did not. Leung et al., *Science* 246:1306 (1989). Thus, the native VEGF dimer is known to promote vascular endothelial cell proliferation and angiogenesis, a process which involves the formation of new blood vessels from preexisting endothelium. As such, the native VEGF may be useful for the therapeutic treatment of numerous conditions in which a growth-promoting activity on the vascular endothelial cells is important, for example, in ulcers, vascular injuries and myocardial infarction. The endothelial cell proliferative activity of the VEGF dimer is known to be mediated by two high affinity tyrosine kinase receptors, flt-1 (FMS-like tyrosine kinase) and KDR (kinase domain region), which exist only on the surface of vascular endothelial cells. DeVries, et al., *Science* 225:989–991 (1992) and Terman, et al., *Oncogene* 6:1677–1683 (1991). As cells become depleted in oxygen, because of trauma and the like, VEGF production increases in such cells, wherein the generated VEGF protein subsequently binds to its respective cell surface receptors in order to signal ultimate biological effect. The signal then increases vascular permeability and the cells divide and expand to form new vascular pathways. Thus, native VEGF functions to induce vascular proliferation through the binding to endothelial cell-specific receptors.

While VEGF-induced vascular endothelial cell proliferation is desirable under certain circumstances, vascular endothelial cell proliferation and angiogenesis are also important components of a variety of diseases and disorders. Such diseases and disorders include tumor growth and metastasis, rheumatoid arthritis, psoriasis, atherosclerosis, diabetic retinopathy, retrolental fibroplasia, neovascular glaucoma, age-related macular degeneration, hemangiomas, immune rejection of transplanted corneal tissue and other tissues, and chronic inflammation. Obviously, in individuals suffering from any of these disorders, one would want to have a means for inhibiting, or at least substantially reducing, the endothelial cell proliferating activity of the native VEGF dimeric protein.

Having an available means for inhibiting native VEGF activity is important for a number of reasons. For example, in the specific case of tumor cell growth, angiogenesis appears to be crucial for the transition from hyperplasia to neoplasia and for providing nourishment to the growing solid tumor. Folkman, et al., *Nature* 339:58 (1989). Angiogenesis also allows tumors to be in contact with the vascular bed of the host, which may provide a route for metastasis of tumor cells. Evidence for the role of angiogenesis in tumor metastasis is provided, for example, by studies showing a correlation between the number and density of microvessels in histologic sections of invasive human breast carcinoma and actual presence of distant metastasis. Weidner et al., *New Engl. J. Med.* 324:1 (1991). Thus, one possible mechanism for the effective treatment of neoplastic tumors is to inhibit or substantially reduce the endothelial cell proliferative and angiogenic activity of the native dimeric VEGF protein.

Therefore, in view of the role that VEGF-induced vascular endothelial cell growth and angiogenesis play in many diseases and disorders, it is desirable to have a means for reducing or substantially inhibiting one or more of the biological effects of the native VEGF protein, for example, the mitogenic or angiogenic effect thereof. Thus, the present invention is predicated upon research intended to identify novel VEGF variant polypeptides which are capable of inhibiting one or more of the biological activities of native VEGF. Specifically, the present invention is predicated upon the identification of VEGF variants which are capable of binding to and occupying cell-surface VEGF receptors without inducing a typical VEGF response, thereby effectively reducing or substantially inhibiting the effects of native VEGF. It was postulated that if one could prepare such VEGF variants, one could use such variants in instances of tumor treatment in order to starve the tumors for intended regression.

It was a further object of this research to produce VEGF variants which lose the ability to properly dimerize through the formation of covalent cysteine-cysteine disulfide bonds. Such variants include variant VEGF monomers which lack the ability to dimerize through the formation of cysteine-cysteine disulfide bonds and variant VEGF monomers which may dimerize through the formation of at least one cysteine-cysteine disulffide bond, however, wherein at least one disulfide bond differs from that existing in the native VEGF dimer. Such variants possess the ability to bind to and occupy cell surface VEGF receptors without inducing a VEGF response, thereby competing with native VEGF for binding to the receptors and antagonistically inhibiting the biological activity of the native VEGF dimer.

As further objects, the VEGF variants of the present invention can be employed in assays systems to discover small molecule agonists and antagonists for intended therapeutic use.

The results of the above described research is the subject of the present invention. We herein demonstrate that mutation or modification of the cysteine residues at amino acid positions 51 and/or 60 of the native VEGF amino acid sequence functions to produce VEGF variants which lose the ability to properly dimerize. Specifically, substitution of cysteine at positions 51 and/or 60 with another amino acid or modification of the cysteine at that site prevents the ability of that amino acid to participate in the formation of a disulfide bond. These variants, however, retain the ability to bind to and occupy cell surface VEGF receptors without inducing a VEGF response, thereby effectively inhibiting the biological activity of the native VEGF dimer.

SUMMARY OF THE INVENTION

The present invention provides variants of the native VEGF protein which are capable of binding to a VEGF receptor on the surface of vascular endothelial cells, thereby occupying those binding sites and inhibiting the mitogenic, angiogenic or other biological activities of the native VEGF protein. The novel antagonist molecules of the present invention, therefore, are useful for the treatment of diseases or disorders characterized by undesirable excessive vascularization, including by way of example, tumors, and especially solid malignant tumors, rheumatoid arthriUs, psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation. The antagonists of the present invention are also useful for the treatment of diseases or disorders characterized by undesirable vascular permeability, such as edema associated with brain tumors, ascites associated with malignancies, Meigs' syndrome, lung inflammation, nephrotic syndrome, pericardial effusion (such as that associated with pericarditis) and pleural effusion.

In a preferred embodiment, the variant VEGF polypeptides of the antagonist molecules of the present invention comprise amino acid modifications of at least one cysteine residue present in the native VEGF amino acid sequence wherein modification of that cysteine residue(s) results in the polypeptide being incapable of properly dimerizing with another VEGF polypeptide.

In a particularly preferred embodiment, the cysteine residues of the native VEGF amino acid sequence that are modified are at amino acid positions 51 and/or 60 of the native VEGF amino acid sequence.

The novel VEGF variant polypeptides of the present invention may be recombinantly generated by creating at least one amino acid mutation at a cysteine residue in the native VEGF amino acid sequence such that the variant is incapable of properly dimerizing. Typical mutations include, for example, substitutions, insertions and/or deletions. The cysteine residue(s) of interest may also be chemically modified so as to be incapable of participating in a disulfide bond.

In other embodiments, the present invention is directed to isolated nucleic acid sequences encoding the novel VEGF antagonist molecules of the present invention and replicable expression vectors comprising those nucleic acid sequences.

In still other embodiments, the present invention is directed to host cells which are transfected with the replicable expression vectors of the present invention and are capable of expressing those vectors.

In yet another embodiment, the present invention is directed to a composition for treating indications wherein anti-angiogenesis is desired, such as in arresting tumor growth, comprising a therapeutically effective amount of the antagonist molecule of the present invention compounded with a pharmaceutically acceptable carrier. Another embodiment of the present invention is directed to a method of treating comprising administering a therapeutically effective amount of the above described composition.

Expanding on the basic premise hereof of the discovery and mutagenesis of the native VEGF polypeptide to produce variant VEGF polypeptides, the present invention is directed to all associated embodiments deriving therefro m, including recombinant DNA materials and processes for preparing such variants, materials and information for compounding such variants into pharmaceutically finished form and assays using such variants to screen for candidates that have agonistic or antagonistic properties with respect to the native VEGF polypeptide.

BRIEF DESCRIPTION OF THE DRAWINGS

FIG. 1A and 1B depict both the amino acid and DNA sequence for a native VEGF protein having 165 amino acids. Predicted amino acids of the protein are shown below the DNA sequence and are numbered from the first residue of the N-terminus of the protein sequence. Negative amino acid numbers refer to the presumed leader signal sequence or pre-protein, while positive numbers refer to the putative mature protein.

DETAILED DESCRIPTION OF THE INVENTION

Figure 2:
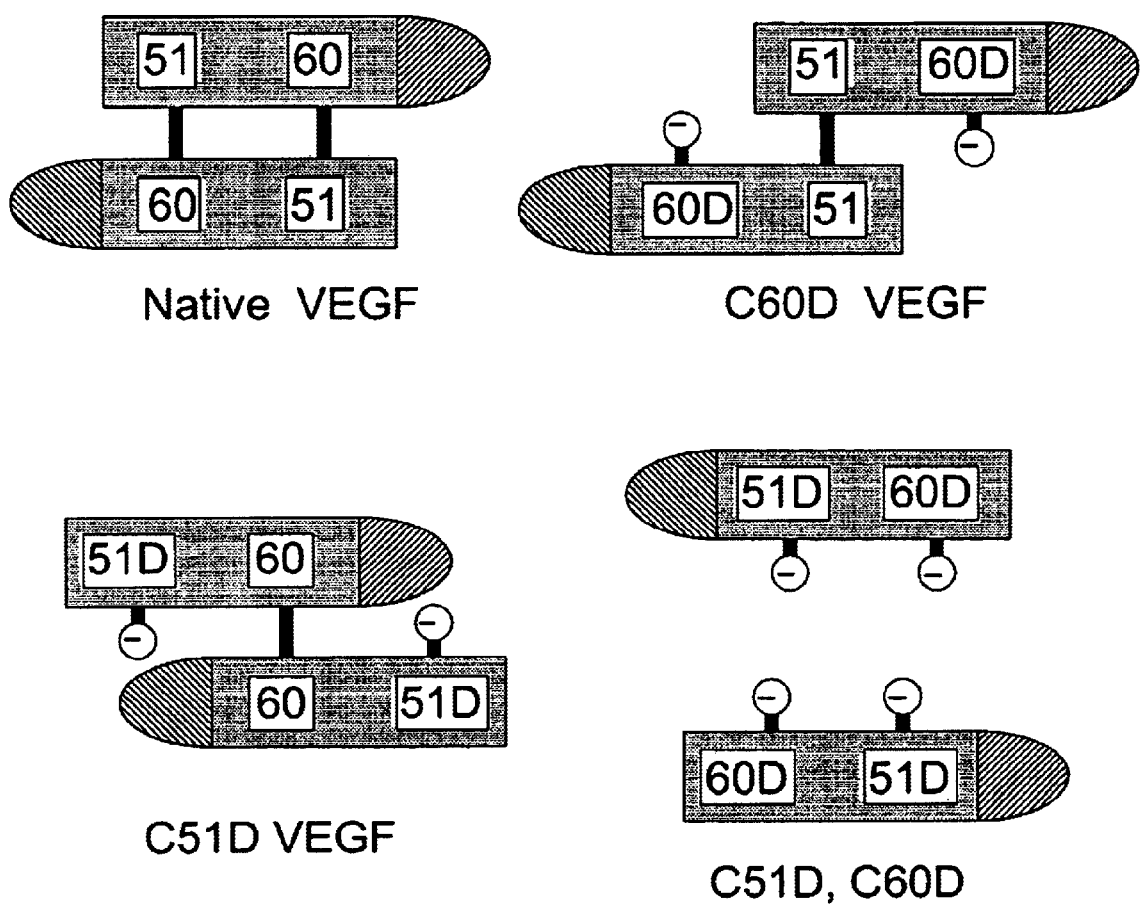
FIG. 2 is a schematic diagram showing the native VEGF dimer molecule having disulfide bonds between cysteine residues at amino acid positions 51 and 60 and 60 and 51, respectively, of the monomeric units, variant polypeptide C51D, wherein the cysteine residue at amino acid position 51 has been substituted by an aspartic acid residue resulting in the formation of a staggered dimer, variant polypeptide C60D, wherein the cysteine residue at amino acid position 60 has been substituted by an aspartic acid residue resulting in the formation of a staggered dimer and variant polypeptide C51D, C60D, wherein the cysteine residues at both amino acid positions 51 and 60 have been substituted by aspartic acid residues, thereby preventing disulfide bond formation and dimerization.

As used herein, "vascular endothelial cell growth factor," or "VEGF," refers to a native mammalian growth factor as defined in U.S. Pat. No. 5,332,671, including the human amino acid sequence shown in FIG. 1 and naturally occurring allelic and processed forms of such growth factors. VEGF proteins can exist in either monomeric or multimeric (for example, dimeric) form. "Proper dimerization" is the dimerization which normally occurs between native VEGF monomers.

The term "native" with regard to a VEGF protein refers to a naturally occurring VEGF protein of any human or non-human animal species, with or without the initiating methionine, whether purified from the native source, synthesized, produced by recombinant DNA technology or by any combination of these and/or other methods. Native VEGF proteins naturally exist as dimeric molecules, wherein the monomeric units thereof are covalently connected through the formation of cysteine-cysteine disulfide bonds. Native VEGF specifically includes the native human VEGF protein having the amino acid sequence shown in FIG. 1 and possesses the ability to induce the proliferation of vascular endothelial cells in vivo.

The term "variant" with respect to a VEGF protein refers to a VEGF protein that possesses at least one amino acid mutation or modification (i.e., alteration) as compared to a native VEGF protein and which may or may not lack one or more of the biological activities of a native VEGF protein. Variant VEGF proteins generated by "amino acid modifications" can be produced, for example, by substituting, deleting, inserting and/or chemically modifying at least one amino acid in the native VEGF amino acid sequence. Methods for creating such VEGF variants are described below.

The term "monomeric vaiant", "monomeric antagonist" or grammatical equivalents thereof refers to a variant VEGF protein having at least one amino acid alteration as compared to a native VEGF monomer, wherein said amino acid alteration acts to prevent dimer formation between the monomeric units. Thus, the "monomeric variants" or "monomeric antagonists" of the present invention are those VEGF variants which are incapable of dimerizing through the formation of cysteine-cysteine disulfide bonds. Monomeric variants of the native VEGF pro tein, however, will possess the ability to bind to and occupy cell-surface VEGF receptors without inducing a mitogenic and/or angiogenic VEGF response, although the binding affinity of the monomeric variant at those receptors may differ from that of a native VEGF protein.

The term "staggered dimer", "staggered antagonist" or grammatical equivalents thereof refers to a variant VEGF protein having at least one amin o acid alteration as compared to a native VEGF protein and which retains the ability to dimerize through the formation of at least one cysteine-cysteine disulfide bond, however, where at least one of the disulfide bonds formed is different from that which exists in the native VEGF dimeric protein.

A "functional derivative" of a polypeptide is a compound having a qualitative biological activity, or lack thereof, in common with the another polypeptide. Thus, for example, a functional derivative of a VEGF antagonist compound of the present invention is a compound that has a qualitative biological activity in common with an original polypeptide antagonist, for example, as being capable of binding to cell surface VEGF receptors without inducing a VEGF response, thereby occupying those receptors and inhibiting native VEGF activity. "Functional derivatives" include, but are not limited to, amino acid sequence variants of the variant VEGF proteins of the present invention, fragments of polypeptides from any animal species (including humans), derivatives of human and non-human polypeptides and their fragments, and peptide analogs of native polypeptides, provided that they have a biological activity, or lack thereof, in common with a respective variant VEGF protein. "Fragments" comprise regions within the sequence of a mature polypeptide. The term "derivative" is used to define amino acid sequence variants, and covalent modifications of a polypeptide.

"Identity" or "homology" with respect to a polypeptide and/or its functional derivatives is defined herein as the percentage of amino acid residues in the candidate sequence that are identical with the residues of a corresponding polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known in the art.

The term "biological activity" in the context of the definition of functional derivatives is defined as the possession of at least one function qualitatively in common with another polypeptide. The functional derivatives of the polypeptide antagonists of the present invention are unified by their qualitative ability to bind to a VEGF receptor without inducing a VEGF response, thereby preventing native VEGF from binding at that site and, in turn, inhibiting the biological activity of the native VEGF protein.

The term "antagonist" is used to refer to a molecule inhibiting a biological activity of a native VEGF protein.

Preferably, the VEGF antagonist compounds herein inhibit the ability of VEGF to induce vascular endothelial cell proliferation. Preferred antagonists essentially completely inhibit vascular endothelial cell proliferation.

Ordinarily, the terms "amino acid" and "amino acids" refer to all naturally occurring L-α-amino acids. In some embodiments, however, either D-amino acids or non-natural substituted amino acids may be present in the polypeptides or peptides of the present invention in order to facilitate conformational restriction. For example, in order to facilitate disulfide bond formation and stability, a D-amino acid cysteine may be provided at one or both termini of a peptide functional derivative or peptide antagonist of the native VEGF protein. The amino acids are identified by either the single-letter or three-letter designations:

| Asp | D | aspartic acid | Ile | I | isoleucine |
|---|---|---|---|---|---|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids

Acidic Residues: aspartic acid, glutamic acid
Basic Residues: lysine, arginine, histidine II. Uncharged Amino Acids Hydrophilic Residues: serine, threonine, asparagine, glutamine
Aliphatic Residues: glycine, alanine, valine, leucine, isoleucine
Non-polar Residues: cysteine, methionine, proline
Aromatic Residues: phenylalanine, tyrosine, tryptophan The term "amino acid sequence variant" or "amino acid alteration" refers to molecules having at (east one differences in their amino acid sequence as compared to another amino acid sequence, usually the native amino acid sequence.

"Substitutional" variants are those that have at least one amino acid residue in a corresponding sequence removed and a different amino acid inserted in its place at the same position. The substitutions may be single, where only one amino acid in the molecule has been substituted, or they may be multiple, where two or more amino acids have been substituted in the same molecule.

"Insertional" variants are those with one or more amino acids inserted immediately adjacent to an amino acid at a particular position in a corresponding sequence. Immediately adjacent to an amino acid means connected to either the α-carboxy or α-amino functional group of the amino acid.

"Deletional" variants are those with one or more amino acids in a corresponding amino acid sequence removed. Ordinarily, deletional variants will have one or two amino acids deleted in a particular region of the molecule.

The term "isolated" means that a nucleic acid or polypeptide is identified and separated from contaminant nucleic acids or polypeptides present in the animal or human source of the nucleic acid or polypeptide.

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50° C., or (2) employing during hybridization a denaturing agent, such as formamide, for example, 50% (vol/vol) formamide with 0.1% bovine serum albumin/0.1% Ficoll/0.1% polyvinylpyrrolidone/50 nM sodium phosphate buffer at pH 6.5 with 750 mM sodium chloride, 75 mM sodium citrate at 42° C. Another example is use of 50% formamide, 5×SSC (0.75 M NaCl, 0.075 M sodium citrate), 50 mM sodium phosphate (pH 6/8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS. Yet another example is hybridization using a buffer of 10% dextran sulfate, 2×SSC (sodium chloride/sodium citrate) and 50% formamide at 55° C., followed by a high-stringency wash consisting of 0.1×SSC containing EDTA at 55° C.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, S. N. *Proc. Natl. Acad. Sci.* (*USA*), 69, 2110 (1972) and Mandel et al. *J. Mol. Biol.* 53, 154 (1 970), is generally used for prokaryotes or other cells that contain substantial cell-wall barriers. For mammalian cells without such cell walls, the calcium phosphate precipitation method of Graham, F. and van der Eb, A., *Virology*, 52, 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, P., et al. *J. Bact.*, 130, 946 (1977) and Hsiao, C. L., et al. *Proc. Natl. Acad. Sci.* (*USA*) 76, 3829 (1979). However, other methods for introducing DNA into cells such as by nuclear injection or by protoplast fusion may also be used.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the single-stranded phage DNA, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. Plaques of interest are selected by hybridizing with kinased synthetic primer at a temperature that permits hybridization of an exact match, but at which the mismatches with the original strand are sufficient to prevent hybridization. Plaques that hybridize with the probe are then selected, sequenced and cultured, and the DNA is recovered.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accord with conventional practice.

"Control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 mg of plasmid or DNA fragment is used with about 1–2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al. 1982, *Molecular Cloning: A Laboratory Manual* (New York: Cold Spring Harbor Laboratory, 1982) pp. 133–134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., *Nucleic Acids Res.* 9, 6103–6114 (1981), and D. Goeddel et al., *Nucleic Acids Res.* 8, 4057 (1980).

"Ligation" refers to the process of forming phosphodiester bonds between two double stranded nucleic acid fragments (T. Maniatis et al. 1982, supra, p. 146). Unless otherwise provided, ligation may be accomplished using known buffers and conditions with 10 units of T4 DNA ligase ("ligase") per 0.5 mg of approximately equimolar amounts of the DNA fragments to be ligated.

"Preparation" of DNA from transformants means isolating plasmid DNA from microbial culture. Unless otherwise provided, the alkaline/SDS method of Maniatis et al. 1982, supra, p. 90, may be used.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP Pat. Pub. No. 266,032 published May 4, 1988, or via deoxynucleoside H-phosphonate intermediates as described by Froehler et al., *Nucl. Acids Res.* 14, 5399–5407 [1986]). They are then purified on polyacrylamide gels.

The abbreviation "KDR" refers to the kinase domain region of the VEGF molecule, whether a native VEGF molecule or a variant thereof. It is this region which is known to bind to the kinase domain region receptor.

The abbreviation "FLT-1" refers to the FMS-like tyrosine kinase binding domain which is known to bind to the corresponding flt-1 receptor. These receptors exist on the surfaces of endothelial cells.

B. General Methodology

1. Glycosylation

The VEGF variants of the present invention may contain at least one amino acid sequence that has the potential to be glycosylated through an N-linkage and that is not normally glycosylated in the native VEGF molecule.

Introduction of an N-linked glycosylation site in the variant requires a tripeptidyl sequence of the formula: asparagine-X-serine or asparagine-X-threonine, wherein asparagine is the acceptor and X is any of the twenty genetically encoded amino acids except proline, which prevents glycosylation. See D. K. Struck and W. J. Lennarz, in *The Biochemistry of Glycoproteins and Proteoglycans*, ed. W. J. Lennarz, Plenum Press, 1980, p. 35; R. D. Marshall, *Biochem. Soc. Symp.*, 40, 17 (1974), and Winzler, R. J., in *Hormonal Proteins and Peptides* (ed. Li, C.I . p. 1–1 5 (Academic Press, New York, 1973). The amino acid sequence variant herein is modified by substituting for the amino acid(s) at the appropriate site(s) the appropriate amino acids to effect glycosylation.

If O-linked glycosylation is to be employed, O-glycosidic linkage occurs in animal cells between N-acetylgalactosamine, galactose, or xylose and one of several hydroxyamino acids, most commonly serine or threonine, but also in some cases a 5-hydroxyproline or 5-hydroxylysine residue placed in the appropriate region of the molecule.

Glycosylation patterns for proteins produced by mammals are described in detail in *The Plasma Proteins: Structure, Function and Genetic Control*, F. W. Putnam, ed., 2nd edition, volume 4 (Academic Press, New York, 1984), p. 271–315, the entire disclosure of which is incorporated herein by reference. In this chapter, asparagine-linked oligosaccharides are discussed, including their subdivision into at least three groups referred to as complex, high mannose, and hybrid structures, as well as O-glucosidically linked oligosaccharides.

Chemical and/or enzymatic coupling of glycosides to proteins can be accomplished using a variety of activated groups, for example, as described by Aplin and Wriston in *CRC Crit. Rev. Biochem.*, pp. 259–306 (1981), the disclosure of which is incorporated herein by reference. The advantages of the chemical coupling techniques are that they are relatively simple and do not need the complicated enzymatic machinery required for natural O- and N-linked glycosylation. Depending on the coupling mode used, the sugar(s) may be attached to (a) arginine or histidine, (b) free carboxyl groups such as those of glutamic acid or aspartic acid, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described more fully in PCT WO 87/05330 published Sep. 11, 1987, the disclosure of which is incorporated herein by reference.

Glycosylation patterns for proteins produced by yeast are described in detail by Tanner and Lehle, *Biochim. Biophys. Acta*, 906(1), 81–99 (1987) and by Kukuruzinska et al., *Annu. Rev. Biochem.*, 56, 915–944 (1987), the disclosures of which are incorporated herein by reference.

2. Amino Acid Sequence Variants a. Additional Mutations

For purposes of shorthand designation of the VEGF variants described herein, it is noted that numbers refer to the amino acid residue/position along the amino acid sequences of the putative mature VEGF protein shown in FIGS. 1A and 1B.

The present invention is directed to variants of VEGF where such variants have modifications in the amino acid sequence that affect the ability of the EGF monomeric units to properly dimerize. These variants have the ability to bind to and occupy cell-surface VEGF receptors without substantially activating vascular endothelial proliferation and angiogenesis, thereby inhibiting the biological activity of native VEGF. Specifically, amino acid modifications can be made at amino acid positions 51 and/or 60, each of which affect the ability of the variant VEGF monomers to properly dimerize. Moreover, additional variants based upon these original variants can be made by means generally known well in the art and without departing from the spirit of the present invention.

With regard to the VEGF variants of the present invention, for example, covalent modifications can be made to various of the amino acid residues.

b. DNA Mutations

Amino acid sequence variants of VEGF and variants thereof can also be prepared by mutations in the DNA. Such variants include, for example, deletions from, or insertions or substitutions of, residues within the amino acid sequence shown in FIG. 1. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP 75,444A).

At the genetic level, these variants ordinarily are prepared by site-directed mutagenesis of nucleotides in the DNA encoding the VEGF, thereby producing DNA encoding the variant, and thereafter expressing the DNA in recombinant cell culture.

While the site for introducing an amino acid sequence variation is predetermined, the mutation per se need not be predetermined. For example, to optimize the performance of a mutation at a given site, random mutagenesis may be conducted at the target codon or region and the expressed VEGF variants screened for the optimal combination of desired activity. Techniques for making substitution mutations at predetermined sites in DNA having a known sequence are well known, for example, site-specific mutagenesis.

Preparation of VEGF variants in accordance herewith is preferably achieved by site-specific mutagenesis of DNA that encodes an earlier prepared variant or a nonvariant version of the protein. Site-specific mutagenesis allows the production of VEGF variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2, 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol*., 153, 3 [1987]) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (*USA*), 75, 5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

c. Types of Mutations

Amino acid sequence deletions generally range from about 1 to 30 residues, more preferably 1 to 10 residues, and typically are contiguous.

Amino acid sequence insertions include amino- and/or carboxyl-terminal fusions of from one residue to polypeptides of essentially unrestricted length, as well as intrasequence insertions of single or multiple amino acid residues. Intrasequence insertions (i.e., insertions within the mature VEGF sequence) may range generally from about 1 to 10 residues, more preferably 1 to 5. An example of a terminal insertion includes a fusion of a signal sequence, whether heterologous or homologous to the host cell, to the N-terminus of the variant VEGF molecule to facilitate the secretion of variant VEGF from recombinant hosts.

The third group of variants are those in which at least one amino acid residue in the VEGF molecule, and preferably only one, has been removed and a different residue inserted in its place. Such substitutions preferably are made in accordance with the following Table 1 when it is desired to modulate finely the characteristics of a VEGF molecule or variant thereof.

TABLE 1

| Original Residue | Exemplary Substitutions |
| --- | --- |
| Ala (A) | gly; ser |
| Arg (R) | lys |
| Asn (N) | gln; his |
| Asp (D) | glu |
| Cys (C) | ser |
| Gln (Q) | asn |
| Glu (E) | asp |
| Gly (G) | ala; pro |
| His (H) | asn; gln |
| Ile (I) | leu; val |
| Leu (L) | ile; val |
| Lys (K) | arg; gln; glu |
| Met (M) | leu; tyr; ile |
| Phe (F) | met; leu; tyr |
| Ser (S) | thr |
| Thr (T) | ser |
| Trp (W) | tyr |
| Tyr (Y) | trp; phe |
| Val (V) | ile; leu |

Substantial changes in function or immunological identity are made by selecting substitutions that are less conservative than those in Table I, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in biological properties will be those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; (e) a residue having an electronegative side chain is substituted for (or by) a residue having an electropositive charge; or (f) a residue having a bulky side chain, e.g., phenylalanine, is substituted for (or by) one not having such a side chain, e.g., glycine.

Most deletions and insertions, and substitutions in particular, are not expected to produce radical changes in the characteristics of the VEGF molecule or variant thereof. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native VEGF-encoding nucleic acid, expression of the variant nucleic acid in recombinant cell culture, and, optionally, purification from the cell culture, for example, by immunoaffinity adsorption on a rabbit polyclonal anti-VEGF column (to absorb the variant by binding it to at least one remaining immune epitope).

Since VEGF tends to aggregate into dimers, it is within the scope hereof to provide hetero- and homodimers, wherein one or both subunits are variants. Where both subunits are variants, the changes in amino acid sequence can be the same or different for each subunit chain. Heterodimers are readily produced by cotransforming host cells with DNA encoding both subunits and, if necessary, purifying the desired heterodimer, or by separately synthesizing the subunits, dissociating the subunits (e.g., by treatment with a chaotropic agent such as urea, guanidine hydrochloride, or the like), mixing the dissociated subunits, and then reassociating the subunits by dialyzing away the chaotropic agent.

Also included within the scope of mutants herein are so-called glyco-scan mutants. This embodiment takes advantage of the knowledge of so-called glycosylation sites which are identified by the sequence—NX(S/T) wherein N represents the amino acid asparagine, X represents any amino acid except proline and probably glycine and the third position can be occupied by either amino acid serine or threonine. Thus, where appropriate, such a glycosylation site can be introduced so as to produce a species containing glycosylation moieties at that position. Similarly, an existing glycosylation site can be removed by mutation so as to produce a species that is devoid of glycosylation at that site. It will be understood, again, as with the other mutations contemplated by the present invention, that they are introduced at amino acid position(s) 51 and/or 60 of the native VEGF amino acid sequence in accord with the basic premise of the present invention, and they can be introduced at other locations outside of these amino acid positions within the overall molecule so long as the final product does not differ in overall kind from the properties of the original VEGF variant.

The activity of the cell lysate or purified VEGF variant is then screened in a suitable screening assay for the desired characteristic. For example, binding to the cell-surface VEGF receptor can be routinely assayed by employing well known VEGF binding assays such as those described in the Examples below. A change in the immunological character of the VEGF molecule, such as affinity for a given antibody, is measured by a competitive-type immunoassay. Changes in the enhancement or suppression of vascular endothelium growth by the candidate variants are measured by the appropriate assay (see Examples below). Modifications of such protein properties as redox or thermal stability, hydrophobicity, susceptibility to proteolytic degradation, or the tendency to aggregate with carriers or into multimers are assayed by methods well known to the ordinarily skilled artisan.

3. Recombinant Expression

The variant VEGF molecule desired may be prepared by any technique, including by recombinant methods. Likewise, an isolated DNA is understood herein to mean chemically synthesized DNA, cDNA, chromosomal, or extrachromosomal DNA with or without the 3'- and/or 5'-flanking regions. Preferably, the desired VEGF variant herein is made by synthesis in recombinant cell culture.

For such synthesis, it is first necessary to secure nucleic acid that encodes a VEGF molecule. DNA encoding a VEGF molecule may be obtained from bovine pituitary follicular cells by (a) preparing a cDNA library from these cells, (b) conducting hybridization analysis with labeled DNA encoding the VEGF or fragments thereof (up to or more than 100 base pairs in length) to detect clones in the library containing homologous sequences, and (c) analyzing the clones by restriction enzyme analysis and nucleic acid sequencing to identify full-length clones. DNA encoding a VEGF molecule from a mammal other than bovine can also be obtained in a similar fashion by screening endothelial or leukemia cell libraries. DNA that is capable of hybridizing to a VEGF-encoding DNA under low stringency conditions is useful for identifying DNA encoding VEGF. Both high and low stringency conditions are defined further below. If full-length clones are not present in a cDNA library, then appropriate fragments may be recovered from the various clones using the nucleic acid sequence information disclosed herein for the first time and ligated at restriction sites common to the clones to assemble a full-length clone encoding the VEGF molecule. Alternatively, genomic libraries will provide the desired DNA.

Once this DNA has been identified and isolated from the library it is ligated into a replicable vector for further cloning or for expression.

In one example of a recombinant expression system a VEGF-encoding gene is expressed in mammalian cells by transformation with an expression vector comprising DNA encoding the VEGF. It is preferable to transform host cells capable of accomplishing such processing so as to obtain the VEGF in the culture medium or periplasm of the host cell, i.e., obtain a secreted molecule.

a. Useful Host Cells and Vectors

The vectors and methods disclosed herein are suitable for use in host cells over a wide range of prokaryotic and eukaryotic organisms.

In general, of course, prokaryotes are preferred for the initial cloning of DNA sequences and construction of the vectors useful in the invention. For example, *E. coil* K12 strain MM 294 (ATCC No. 31,446) is particularly useful. Other microbial strains that may be used include *E. coli* strains such as *E. coli* B and *E. coli* X1776 (ATCC No. 31,537). These examples are, of course, intended to be illustrative rather than limiting.

Prokaryotes may also be used for expression. The aforementioned strains, as well as *E. coli* strains W3110 (F-, lambda-, prototrophic, ATCC No. 27,325), K5772 (ATCC No. 53,635), and SR101, bacilli such as *Bacillus subtilis*, and other enterobacteriaceae such as *Salmonella typhimurium* or *Serratia marcesans*, and various pseudomonas species, may be used.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene* 2, 95 [1977]). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems (Chang et al., *Nature*, 375, 615 [1978]; Itakura et al., *Science*, 198, 1056 [1977]; Goeddel et al., *Nature*, 281, 544 [1979]) and a tryptophan (trp) promoter system (Goeddel et al., *Nucleic Acids Res.*, 8, 4057 [1980]; EPO Appl. Publ. No. 0036,776). While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell*, 20, 269 [1980]).

In addition to prokaryotes, eukaryotic microbes, such as yeast cultures, may also be used. *Saccharomvces cerevisiae*, or common baker's yeast, is the most commonly used among eukaryotic microorganisms, although a number of other strains are commonly available. For expression in Saccharomyces, the plasmid YRp7, for example (Stinchcomb et al., *Nature* 282, 39 [1979]; Kingsman et al., *Gene* 7, 141 [1979]; Tschemper et al., *Gene* 10, 157 [1980]), is commonly used. This plasmid already contains the trp1 gene that provides a selection marker for a mutant strain of yeast lacking the ability to grow in tryptophan, for example, ATCC No. 44,076 or PEP4-1 (Jones, *Genetics*, 85, 12 [1977]). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.* 255, 2073 [1980]) or other glycolytic enzymes (Hess et al., *J. Adv. Enzyme Reg.* 7, 149 [1968]; Holland et al., *Biochemistry* 17, 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication [Fiers et al., *Nature*, 273, 113 (1978)]. Smaller or larger SV40 fragments may also be used, provided there is included the approximately 250-bp sequence extending from the HindIII site toward the BgII site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

In selecting a preferred host cell for transfection by the vectors of the invention that comprise DNA sequences encoding both VEGF and DHFR protein, it is appropriate to select the host according to the type of DHFR protein employed. If wild-type DHFR protein is employed, it is preferable to select a host cell that is deficient in DHFR; thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci. (USA)* 77, 4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

b. Typical Methodology Employable

Construction of suitable vectors containing the desired coding and control sequences employs standard ligation techniques. Isolated plasmids or DNA fragments are cleaved, tailored, and religated in the form desired to prepare the plasmids required.

If blunt ends are required, the preparation may be treated for 15 minutes at 15° C. with 10 units of Polymerase I (Klenow), phenol-chloroform extracted, and ethanol precipitated.

Size separation of the cleaved fragments may be performed using 6 percent polyacrylamide gel described by Goeddel et al., *Nucleic Acids Res.* 8, 4057 (1980).

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.* 9, 309 (1981) or by the method of Maxam et al., *Methods of Enzymology* 65, 499 (1980).

After introduction of the DNA into the mammalian cell host and selection in medium for stable transfectants, amplification of DHFR-protein-coding sequences is effected by growing host cell cultures in the presence of approximately 20,000–500,000 nM concentrations of methotrexate, a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

Other techniques employable are described in a section just prior to the examples.

4. Utilities and Formulation

The variant VEGF antagonists of the present invention have a number of therapeutic uses associated with the vascular endothelium. Such uses include, for example, incorporation into formed articles which can be used in modulating endothelial cell growth and angiogenesis. In addition, tumor invasion and metastasis may be modulated with these articles. Other disorders for which the polypeptides of the present invention may find use are discussed supra.

For the indications referred to above, the variant VEGF antagonist molecule will be formulated and dosed in a fashion consistent with good medical practice taking into account the specific disease or disorder to be treated, the condition of the individual patient, the site of delivery of the VEGF antagonist, the method of administration, and other factors known to practitioners. Thus, for purposes herein, the "therapeutically effective amount" of the VEGF is an amount that is effective either to prevent, lessen the worsening of, alleviate, or cure the treated condition, in particular that amount which is sufficient to substantially inhibit the growth of vascular endothelium in vivo. VEGF amino acid sequence variants and derivatives that are immunologically crossreactive with antibodies raised against native VEGF are useful in immunoassays for VEGF as standards, or, when labeled, as competitive reagents.

The VEGF antagonist is prepared for storage or administration by mixing VEGF antagonist having the desired degree of purity with physiologically acceptable carriers, excipients, or stabilizers. Such materials are non-toxic to recipients at the dosages and concentrations employed. If the VEGF antagonist is water soluble, it may be formulated in a buffer such as phosphate or other organic acid salt preferably at a pH of about 7 to 8. If a VEGF variant is only partially soluble in water, it may be prepared as a microemulsion by formulating it with a nonionic surfactant such as Tween, Pluronics, or PEG, e.g., Tween 80, in an amount of 0.04–0.05% (w/v), to increase its solubility.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

The VEGF antagonist to be used for therapeutic administration must be sterile. Sterility is readily accomplished by filtration through sterile filtration membranes (e.g., 0.2 micron membranes). The VEGF ordinarily will be stored in lyophilized form or as an aqueous solution if it is highly stable to thermal and oxidative denaturation. The pH of the VEGF antagonist preparations typically will be about from 6 to 8, although higher or lower pH values may also be appropriate in certain instances. It will be understood that use of certain of the foregoing excipients, carriers, or stabilizers will result in the formation of salts of the VEGF antagonist.

If the VEGF antagonist is to be used parenterally, therapeutic compositions containing the VEGF antagonist generally are placed into a container having a sterile access port, for example, an intravenous solution bag or vial having a stopper pierceable by a hypodermic injection needle.

Generally, where the disorder permits, one should formulate and dose the VEGF for site-specific delivery. This is convenient in the case of site-specific solid tumors.

Sustained release formulations may also be prepared, and include the formation of microcapsular particles and implantable articles. For preparing sustained-release VEGF antagonist compositions, the VEGF antagonist is preferably incorporated into a biodegradable matrix or microcapsule. A suitable material for this purpose is a polylactide, although other polymers of poly-(a-hydroxycarboxylic acids), such as poly-D-(−)-3-hydroxybutyric acid (EP 133,988A), can be used. Other biodegradable polymers include poly(lactones), poly(acetals), poly(orthoesters), or poly(orthocarbonates). The initial consideration here must be that the carrier itself, or its degradation products, is nontoxic in the target tissue and will not further aggravate the condition. This can be determined by routine screening in animal models of the target disorder or, if such models are unavailable, in normal animals. Numerous scientific publications document such animal models.

For examples of sustained release compositions, see U.S. Pat. No. 3,773,919, EP 58,481A, U.S. Pat. No. 3,887,699, EP 158,277A, Canadian Patent No. 1176565, U. Sidman et al., *Biopolymers* 22, 547 [1983], and R. Langer et al., *Chem. Tech.* 12, 98 [1982].

When applied topically, the VEGF antagonist is suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the VEGF antagonist formulated in a liquid composition may be mixed with an effective amount of a water-soluble polysaccharide or synthetic polymer such as polyethylene glycol to form a gel of the proper viscosity to be applied topically. The polysaccharide that may be used includes; for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl-cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the VEGF antagonist held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree-of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2–5%, more preferably about 3%, of the gel and the VEGF antagonist is present in an amount of about 300–1000 mg per ml of gel.

The dosage to be employed is dependent upon the factors described above. As a general proposition, the VEGF antagonist is formulated and delivered to the target site or tissue at a dosage capable of establishing in the tissue a VEGF antagonist level greater than about 0.1 ng/cc up to a maximum dose that is efficacious but not unduly toxic. This intra-tissue concentration should be maintained if possible by continuous infusion, sustained release, topical application, or injection at empirically determined frequencies.

5. Pharmaceutical Compositions

The compounds of the present invention can be formulated according to known methods to prepare pharmaceutically useful compositions, whereby the VEGF antagonists hereof are combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences*, 16th ed., 1980, Mack Publishing Co., edited by Oslo et al. the disclosure of which is hereby incorporated by reference. The VEGF variants herein may be administered parenterally, or by other methods that ensure its delivery to the bloodstream in an effective form.

Compositions particularly well suited for the clinical administration of the VEGF antagonists hereof employed in the practice of the present invention include, for example, sterile aqueous solutions, or sterile hydratable powders such as lyophilized protein. It is generally desirable to include further in the formulation an appropriate amount of a pharmaceutically acceptable salt, generally in an amount sufficient to render the formulation isotonic. A pH regulator such as arginine base, and phosphoric acid, are also typically included in sufficient quantities to maintain an appropriate pH, generally from 5.5 to 7.5. Moreover, for improvement of shelf-life or stability of aqueous formulations, it may also be desirable to include further agents such as glycerol. In this manner, variant t-PA formulations are rendered appropriate for parenteral administration, and, in particular, intravenous administration.

Dosages and desired drug concentrations of pharmaceutical compositions of the present invention may vary depending on the particular use envisioned. For example, "bolus" doses may typically be employed with subsequent administrations being given to maintain an approximately constant blood level, preferably on the order of about 3 µg/ml.

However, for use in connection with emergency medical care facilities where infusion capability is generally not available and due to the generally critical nature of the underlying disease, it will generally be desirable to provide somewhat larger initial doses, such as an intravenous bolus.

For the various therapeutic indications referred to for the compounds hereof, the VEGF antagonists will be formulated and dosed in a fashion consistent with good medical practice taking into account the specific disorder to be treated, the condition of the individual patient, the site of delivery, the method of administration and other factors known to practitioners in the respective art. Thus, for purposes herein, the "therapeutically effective amount" of the VEGF molecules hereof is an amount that is effective either to prevent, lessen the worsening of, alleviate, or cure the treated condition, in particular that amount which is sufficient to substantially reduce or inhibit the growth of vascular endothelium in vivo. In general a dosage is employed capable of establishing in the tissue that is the target for the therapeutic indication being treated a level of a VEGF antagonist hereof greater than about 0.1 ng/cm$^3$ up to a maximum dose that is efficacious but not unduly toxic. It is contemplated that intra-tissue administration may be the choice for certain of the therapeutic indications for the compounds hereof.

The following examples are intended merely to illustrate the best mode now known for practicing the invention but the invention is not to be considered as limited to the details of such examples.

EXAMPLE 1

Materials—Muta-gene phagemid in vitro mutagenesis kit, horse-radish peroxidase conjugated goat IgG specific for murine IgG, pre-stained low-range MW standards and Trans-Blot Transfer Medium (pure nitrocellulose membrane) were purchased from BioRad Laboratories (Richmond, Calif.). Qiagen plasmid Tip 100 kit and Sequenase version 2.0 were from Qiagen (Chatsworth, Calif.) and United States Biochemical (Cleveland, Ohio), respectively. SDS gels (4–20% gradient polyacrylamide) and pre-cut blotting paper were from Integrated Separations Systems (Natick, Mass.). SDS sample buffer (x concentrate) and various restriction enzymes were from New England Biolabs (Beverly, Mass.). O-phenylenediamine, citrate phosphate buffers, sodium dodecyl sulfate, and $H_2O_2$ substrate tablets were purchased from Sigma (St. Louis, Mo.). BufferEZE formula 1 (transfer buffer) and X-OMat AR X-ray film were from Eastman Kodak Co. (Rochester, N.Y.). Maxosorb and Immunlon-1 microtiter plates were purchased from Nunc (Kamstrup, Denmark) and Dynatech (Chantilly, Va.), respectively. Cell culture plates (12-well) and culture media (with calf serum) were from Costar (Cambridge, Mass.) and Gibco (Grand Island, N.Y.), respectively. Polyethylene-20-sorbitan monolaurate (Tween-20) was from Fisher Biotech (Fair Lawn, N.J.). G25 Sephadex columns (PD-10) and $_{125}$I labeled Protein A were from Pharmacia (Piscataway, N.J.) and Amersham (Arlington Heights, Ill.), respectively. Bovine serum albumin (BSA) and rabbit IgG anti-human IgG (Fc-specific) were purchased from Cappel (Durham, N.C.) and Calbiochem (La Jolla, Calif.), respectively. Plasmid vector (pRK5), competent *E. coli* cells (DH5a and CJ236), synthetic oligonucleotides, cell culture medium, purified CHO-derived $VEGF_{165}$, monoclonal (Mates A4.6.1, 2E3, 4D7, SC3, and SF8) and polyclonal antibodies to $VEGF_{165}$ were prepared at Genentech, Inc. (South San Francisco, Calif.). Construction, expression and purification of FLT-1, flkI and KDR receptor-IgG chimeras was as described by Park, et al. *J. Biol. Chem.* 269, 25646–25654 (1994).

Site-directed Mutagenesis and Expression of VEGF Variants—Site-directed mutagenesis was performed using the Muta-Gene Phagemid in vitro mutagenesis kit according to the method of Kunkel *Proc. Natl. Acad. Sci.* 82, 488–492 (1985) and Kunkel et al., *Methods Enzymol.* 154, 367–382 (1987). A plasmid vector pRK5 containing cDNA for $VEGF_{165}$ isoform was used for mutagenesis and transient expression. The pRK5 vector is a modified pUC118 vector and contains a CMV enhancer and promoter [Nakamaye et al., *Nucleic Acids Res.* 14, 9679–9698 (1986) and Vieira et al., *Methods Enzymol.* 155, 3–11 (1987)]. The mutagenized DNA was purified using the Qiagen Plasmid Midi Kit Tip 100 and the sequence of the mutations was verified using Sequenase Version 2.0 Kit. The mutated DNA was analyzed by restriction enzyme digestion as described by Sambrook, et at., *Molecular Cloning*: A Laboratory Manual part I, C5.28–5.32, Cold Spring Harbor Laboratory Press, Cold Spring Harbor, N.Y. (1989).

Transient transfection of human fetal kidney "293 cells" was performed in 6-well plates using the modified calcium phosphate precipitate method as previously described [Jordan et al., *Bio/Technology* (manuscript in preparation) (1994); Chen et al., *Mol. Cell. Biol.* 7, 2745–2752 (1987); Gorman et al., *DNA and Protein Engineering Techniques* 2, 3–10 (1990); Graham et al., *Virology* 52, 456–467 (1973)].

Briefly, approximately 1.2×10⁶ cells were incubated overnight at 37° C. in the presence of 15 μg of precipitated DNA. Cell culture supernatant was replaced with serum free medium, and cell monolayers were incubated for 72 hours at 37° C. Conditioned media (3 ml) was harvested, centrifuged, aliquoted and stored at −70° C. until use.

Quantitation of $VEGF_{165}$ Variants by ELISA—A radioimmunometric assay previously described [Aiello et al., *N. Engl. J. Med.* 331, 1480–1487 (1994)], was adapted for the quantitation of VEGF mutants by the following procedure. Individual wells of a 96-well microtiter plate were coated with 100 μl of a 3 μg/ml solution of an anti-$VEGF_{165}$ polyclonal antibody in 50 mM sodium carbonate buffer pH 9.6 overnight at 4° C. The supernatant was discarded, and the wells were washed 4 times with PBS containing 0.03% Tween 80. The plate was blocked in assay buffer (0.5% BSA, 0.03% Tween 80, 0.01% Thimerosal in PBS) for one hr (300 μl/well) at ambient temperature, then the wells were washed. Diluted samples (100 μl) and $VEGF_{165}$ standard (ranging from 0.1 to 10 ng/ml) were added to each well and incubated for one hr at ambient temperature with gentle agitation. The supernatant was discarded, and the wells were washed. Anti-VEGF murine monoclonal antibody 5F8 solution (100 μl at 1 μg/ml) was added, and the microtiter plate was incubated at ambient temperature for one hr with gentle agitation. After the supernatant was discarded, the plate was washed and horseradish peroxidase conjugated goat IgG specific for murine IgG (100 μl) at a dilution of 1:25000 was immediately added to each well. The plate was incubated for one hr at ambient temperature with gentle agitation after which the supernatant discarded, the wells washed, and developed by addition of orthophenylenediamine (0–04%), $H_2O_2$ (0.012%) in 50 mM citrate phosphate buffer pH 5 (100 μl), then incubated in the dark at ambient temperature for 10 min. The reaction was stopped by adding 50 μl of 4.5 N $H_2SO_4$ to each well and the absorbance was measured at 492 nm on a microplate reader (SLT Labs). The concentrations of $VEGF_{165}$ variants were quantitated by interpolation of a standard curve using non-linear regression analysis. For purposes of comparison, a second ELISA was developed that utilized a dual monoclonal format. The assay was similar to the above described ELISA, except a neutralizing monoclonal antibody (Mab A4.6.1) was used to coat the microtiter plates [Kim et al., *Growth Factors* 7, 53–64 (1992)].

Immunoblotting of VEGF mutants—Aliquots of conditioned cell media (16 μl) containing VEGF or VEGF mutant (approx. 10 ng) were added to ×SDS sample buffer (4 μl) and heated at 90° C. for 3 min prior to loading on SDS polyacrylamide (4 to 20% acrylamide) gels. Pre-stained MW standards (10 μl) were loaded in the outer lanes of the SDS gels. Gels were run at 25 mA for 90 min at 4° C. Gels were transferred to nitrocellulose paper in a Bio-Rad tank blotter containing BufferEZE with 0.1% SDS for 90 min at 250 mA at 25° C. Nitrocellulose was pre-wetted in transfer buffer with 0.1% SDS for 10 min prior to use. Transferred immunoblots were blocked in PBS overnight with 1.0% BSA and 0.1% Tween 20 (blocking buffer) at 4° C. A solution containing 5 murine anti-VEGF Mabs (A.4.6.1, 5C3, 5F8, 4D7, and 2E3) was prepared with 2 μg/ml of each Mab in blocking buffer and used as primary antibody. The primary antibody solution was incubated with the immunoblots for 4 hr at 25° C. with gentle agitation, then washed 3× for 10 min in blocking buffer at 25° C. $^{125}I$ labeled Protein A was diluted to $10^4$ cpm/ml (final concentration) in blocking buffer and incubated with the immunoblots for 60 min with gentle agitation at 25° C. Immunoblots were washed 3× for 10 min in blocking buffer at 25° C., then dried on filter paper and placed on Kodak X-Omat film with two intensifying screens at −70° C. for 3 days.

Preparation of $^{125}I$ labeled $VEGF_{165}$—Radiolabeling of CHO-derived $VEGF_{165}$ was prepared using a modification of the chloramine T catalyzed iodination method [Hunter et al., *Nature* 194, 495–496 (1962)]. In a typical reaction, 10 μl of 1 M Tris-HCl, 0.01% Tween 20 at pH 7.5 was added to 5 μl of sodium iodide-125 (0.5 milliCuries, 0.24 nmol) in a capped reaction vessel. To this reaction, 10 μl of CHO-derived $VEGF_{165}$ (10 μg, 0.26 nmol) was added. The iodination was initiated by addition of 10 μl of 1 mg/ml chloramine T in 0.1 M sodium phosphate, pH 7.4. After 60 sec, iodination was terminated by addition of sodium metabisulfite (20 μl, 1 mg/ml) in 0.1 M sodium phosphate, pH 7.5. The reaction vessel was vortexed after each addition. The reaction mixture was applied to a PD-10 column (G25 Sephadex) that was pre-equilibrated with 0.5% BSA, 0.01% Tween 20 in PBS. Fractions were collected and counted for radioactivity with a gamma scintillation counter (LKB model 1277). Typically, the specific radioactivity of the iodinated VEGF was 26±2.5 μCi/μg, which corresponded to one $^{125}I$ per two molecules of $VEGF_{165}$ dimer.

$VEGF_{165}$ Receptor Birinding Assay—The assay was performed in 96-well immunoplates (Immulon-1); each well was coated with 100 μl of a solution containing 10 μg/ml of rabbit IgG anti-human IgG (Fc-specific) in 50 mM sodium carbonate buffer pH 9.6 overnight at 4° C. After the supernatant was discarded, the wells were washed three times in washing buffer (0.01% Tween 80 in PBS). The plate was blocked (300 μl/well) for one hr in assay buffer (0.5% BSA, 0.03% Tween 80, 0.01% Thimerosal in PBS). The supernatant was discarded and the wells were washed. A cocktail was prepared with conditioned cell media containing $VEGF_{165}$ mutants at varying concentrations (100 μl), $^{125}I$ radiolabeled $VEGF_{165}$ (approx. 5×10₃ cpm in 50 μl) which was mixed with VEGF receptor-IgG chimeric protein, FLT-1 IgG, flk-1 IgG or KDR-IgG (3–15 ng/ml, final concentration, 50 μl) in micronic tubes. Aliquots of this solution (100 pi) were added to pre-coated microtiter plates and incubated for 4 hr at ambient temperature with gentle agitation. The supernatant was discarded, the plate washed, and individual microtiter wells were counted by gamma scintigraphy (LKB model 1277). The competitive binding between unlabeled $VEGF_{165}$ (or $VEGF_{165}$ mutants) and $^{125}I$ radiolabeled $VEGF_{165}$ to the FLT-1, Flk-1, or KDR receptors were plotted, and analyzed using a four parameter fitting program (Kaleidagraph, Adelbeck Software). The apparent dissociation constant for each VEGF mutant was estimated from the concentration required to achieve 50% inhibition ($IC_{50}$).

Assay for Vascular Endothelial Cell Growth—The mitogenic activity of VEGF variants was determined by using bovine adrenal cortical endothelial (ACE) cells as target cells as previously described [Ferrara et al., *Biochem. Biophys. Res. Comm.* 161, 851–859 (1989)]. Briefly, cells were plated sparsely (7000 cells/well) in 12 well plates and incubated overnight in Dulbecco's modified Eagle's medium supplemented with 10% calf serum, 2 mM glutamine, and antibiotics. The medium was exchanged the next day, and VEGF or VEGF mutants, diluted in culture media at concentrations ranging from 100 ng/ml to 10 μg/ml, were layered in duplicate onto the seeded cells. After incubation for 5 days at 37° C., the cells were dissociated with trypsin, and quantified using a Coulter counter.

Isolation of VEGF cDNA

Total RNA was extracted [Ullrich et al., *Science.* 196, 1313–1317 (1977)] from bovine pituitary follicular cells

[obtained as described by Ferrara et al., *Meth. Enzymol.* supra, and Ferrara et al., *Am. J. Physiol.*, supra] and the polyadenylated mRNA fraction was isolated by oligo(dT)-cellulose chromatography. Aviv et al., *Proc. Natl. Acad. Sci. USA* 69, 1408–1412 (1972). The cDNA was prepared [Wickens et al., *J. Biol. Chem.* 253, 2483–2495 (1978)] by priming with $dT_{12-18}$ or a random hexamer $dN_6$.

The double-stranded cDNA was synthesized using a cDNA kit from Amersham, and the resulting cDNA was subcloned into EcoRI-cleaved Igt10 as described [Huynh et al., *DNA Cloning Techniques, A Practical Approach*, Glover ad. (IRL, Oxford, 1985)], except that asymmetric EcoRI linkers [Norris et al., *Gene* 7, 355–362 (1979)] were used, thus avoiding the need for the EcoRI methylase treatment.

The recombinant phage were plated on *E. coli* C600 Hfl [Huynh et al. supra] and replica plated onto-nitrocellulose filters. Benton et al., *Science* 196, 180–182 (1977). These replica were hybridized with a $^{32}$P-labeled [Taylor et al., *Biochim. Biophys. Acta*, 442, 324–330 (1976)] synthetic oligonucleotide probe of the sequence:

5'-CCTATGGCTGAAGGCGGCCAGAAGCCTCACGA AGTGGTGAAGTTCATGGACGTGTATCA-3'$_4$ (SEQ ID NO:1) at 42° C. in 20% formamide, 5×SSC, 50 mM sodium phosphate pH 6.8, 0.1% sodium pyrophosphate, 5×Denhardt's solution, and 50 mg/ml salmon sperm DNA, and washed in 2×SSC, 0.1% SDS at 42° C.

One positive clone, designated I.vegf.6, was identified. This clone, labeled with $^{32}$P, was used asia probe to screen an oligo-dT-primed human placenta cDNA library, and positive clones were observed. When a human pituitary cDNA library was screened with the same labeled clone, no positive clones were detected.

The complete nucleotide sequence of the clone I.vegf.6 was determined by the dideoxyoligonucleotide chain termination method [Sanger et al., *Proc. Natl. Acad. Sci. USA* 74, 5463–5467 (1977)] after subcloning into the pRK5 vector. The sequence obtained, along with the imputed amino acid sequence, including the signal sequence.

Expression of VEGF-Encodina Gene in Mammalian Cells

The final expression vector, pRK5.vegf.6, was constructed from I.vegf.6 and pRK5. The construction of pRK5 and pRK5.vegf.6 is described below in detail.

A. Construction of pRK5

A.1. Construction of PF8CIS

The initial three-part construction of the starting plasmid pF8CIS is described below.

1) The ampicillin resistance marker and replication origin of the final vector was derived from the starting plasmid pUC1 3pML, a variant of the plasmid pML (Lusky, M. and Botchen, M., *Nature*, 293, 79 [1981]). pUC13pML was constructed by transferring the polylinker of pUC13 (Vieira, J. and Messing, J., *Gene*, 19, 259 (1982)) to the EcoRI and HindIII sites of pML. A second starting plasmid pUC8-CMV was the source of the CMV enhancer, promoter and splice donor sequence. pUC8-CMV was constructed by inserting approximately 800 nucleotides for the CMV enhancer, promoter and splice donor sequence into the blunted PstI and SphI sites of pUC8. Vieira, J. and Messing, J., op. cit. Synthetic BamHI-HindIII linkers (commercially available from New England Biolabs) were ligated to the cohesive BamHI end creating a HindIII site. Following this ligation a HindIII-HindII digest was performed. This digest yielded a fragment of approximately 800 bp that contained the CMV enhancer, promoter and splice donor site. Following gel isolation, this 800 bp fragment was ligated to a 2900 bp piece of pUC13pML. The fragment required for the construction of pF8CIS was obtained by digestion of the above intermediate plasmid with SaII and HindIII. This 3123 bp piece contained the resistance marker for ampicillin, the origin of replication from pUC13pML, and the control sequences for the CMV, including the enhancer, promoter, and splice donor site.

2) The 1g variable region intron and splice acceptor sequence was constructed using a synthetic oligomer. A 99 mer and a 30 mer were chemically synthesized having the following sequence for the IgG intron and splice acceptor site (Bothwell et al., *Nature*, 290, 65–67 [1981]):

1 5' AGTAGCAAGCTTGACGTGTGGCAGGCTTGA . . . (SEQ ID NO:2)

31 GATCTGGCCATACACTTGAGTGACAATGA . . . (SEQ ID NO:3)

60 CATCCACTTTGCCTTTCTCTCCACAGGT . . . (SEQ ID NO:4)

88 GTCCACTCCCAG 3' (SEQ ID NO:5)

1 3' CAGGTGAGGGTGCAGCTTGACGTCGTCGGA 5' (SEQ ID NO:6)

DNA polymerase I (Klenow fragment) filled in the synthetic piece and created a double-stranded fragment. Wartell, R. M. and W. S. Reznikoff, *Gene*, 9, 307 (1980). This was followed by a double digest of PstI and HindIII. This synthetic linker was cloned into pUC13 (Veira and Messing, op. cit.) at the PstI and HindIII sites. The clones containing the synthetic oligonucleotide, labeled pUCIg.10, was digested with PstI. A CIaI site was added to this fragment by use of a PstI-CIaI linker. Following digestion with HindIII a 118-bp piece containing part of the Ig intron and the Ig variable region splice acceptor was gel isolated.

3) The third part of the construction scheme replaced the hepatitis surface antigen 3' end with the polyadenylation site and transcription termination site of the early region of SV40. A vector, pUC.SV40, containing the SV40 sequences was inserted into pUC8 at the BamHI site described by Vieira and Messing, op. cit. pUC.SV40 was then digested with EcoRI and HpaI. A 143bp fragment containing the SV40 polyadenylation sequence was gel isolated from this digest. Two additional fragments were gel isolated following digestion of pSVE.8c1 D. (European Pat. Pub. No. 160,457). The 4.8 kb fragment generated by EcoRI and CIaI digestion contains the SV40-DHFR transcription unit, the origin of replication of pML and the ampicillin resistance marker. The 7.5-kb fragment produced following digestion with CIaI and HpaI contains the cDNA for Factor VIII. A three-part ligation yielded pSVE.8c24D. This intermediate plasmid was digested by CIaI and SaII to give a 9611 bp fragment containing the cDNA for Factor VIII with an SV40 poly A site followed by the SV40 DHFR transcription unit.

The final three-part ligation to yield pF8CIS used: a) the 3123 bp SaII-HindIII fragment containing the origin of replication, the ampicillin resistance marker, and the CMV enhancer, promoter, and splice donor site; b) the 11 8 bp HindIII-CIaI fragment containing the Ig intron and splice acceptor site; and c) a 9611 bp CIaI-SaII fragment containing the cDNA for Factor VIII, the SV40 polyadenylation site, and the SV40 DHFR transcription unit.

A.2. Construction of pCIS2.8c28D pCIS2.8c28D comprises a 90 kd subunit of Factor VIII joined to a 73 kd subunit of Factor VIII. The 90 kd comprises amino acids 1 through 740 and the 73 kd subunit amino acids 1690 through 2332. This construct was prepared by a three-part ligation of the following fragments: a) the 12617- bp ClaI-SstII fragment of pF8CIS lisolated from a dam-strain and BAP treated); b) the 216-bp SstII-PstI fragment of pF8CIS; and c) a short PstI-ClaI synthetic oligonucleotide that was kinased.

Two different fragments, A and B, were cloned into the same pUC118 BamHI-PstI BAP vector. The A fragment was the 408bp BamHI-HindIII fragment of pUC408BH and the B fragment was a HindII-PstI oligonucleotide. This oligonucleotide was used without kinasing to prevent its polymerization during ligation.

After ligation of the A and B fragments into the vector, the expected junction sequences were confirmed by DNA sequencing of the regions encompassed by the nucleotides.

The resulting plasmid, pCIS2.8c28D, was constructed with a four-part ligation. The fusion plasmid was cut with BamHI and PstI and the 443 bp fragment isolated. The remaining three fragments of the four-part ligation were: 1) 1944 bp ClaI-BamHI of pSVEFVIII (European Pat. Publ. No. 160,457); 2) a 2202 bp BamHI-XbaI fragment of pSVEFVIII, which was further partially digested with PstI and the 1786 bp PstI-XbaI fragment was isolated, and 3) the 5828 bp XbaI-ClaI BAP fragment of pCIS2.8c24D. The translated DNA sequence of the resultant variant in the exact fusion junction region of pCIS2.8c28D was determined and correlates.

A.3. Construction of pRK5

The starting plasmid for construction of pRK5 was pCIS2.8c28D. The base numbers in paragraphs 1 through 6 refer to pCIS2.8c28D with base one of the first T of the EcoRI site preceding the CMV promoter. The cytomegalovirus early promoter and intron and the SV40 origin and polyA signal were placed on separate plasmids.

1. The cytomegalovirus early promoter was cloned as an EcoRI fragment from pCIS2.8c28D (9999–1201) into the EcoRI site of pUC118 described above. Twelve colonies were picked and screened for the orientation in which single-stranded DNA made from pUC118 would allow for the sequencing from the EcoRI site at 1201 to the EcoRI site at 9999. This clone was named pCMVE/P.

2. Single-stranded DNA was made from pCMVE/P in order to insert an SP6 (Green, M R et al., *Cell* 32, 681–694 [1983]) promoter by site-directed mutagenesis. A synthetic 110 mer that contained the sequences from −69 to +5 of SP6 promoter (see *Nucleic Acids Res.*, 12, 7041 [1984]) were used along with 18-bp fragments on either end of the oligomer corresponding to the CMVE/P sequences. Mutagenesis was done by standard techniques and screened using a labeled 110 mer at high and low stringency. Six potential clones were selected and sequenced. A positive clone was identified-and labeled pCMVE/PSP6.

3. The SP6 promoter was checked and shown to be active, for example, by adding SP6 RNA polyrnerase and checking for RNA of the appropriate size.

4. A CIa-NotI-Sma adapter was synthesized to encompass the location from the ClaI site (91 2) to the SmaI site of pUC 118 in pCMVE/P (step 1) and pCMVE/PSP6 (step 2). This adapter was ligated into the ClaI-SmaI site of pUC118 and screened for the correct clones. The linker was sequenced in both and clones were labeled pCMVE/PSP6-L and pCMVE/P-L.

5. pCMVE/PSP6-L was cut with SmaI (at linker/pUC118 junction) and HindIII (in pUC118). A HpaI (5573)-to-HindIII (6136) fragment from pSVORAADRI 11, described below, was inserted into SmaI-HindIII of pCMVE/PSP6-L. This ligation was screened and a clone was isolated and named pCMVE/PSP6-L-SVORAADRI.

a) The SV40 origin and polyA signal was isolated as the XmnI (5475)-HindIII (6136) fragment from pCIS2.8c28D and cloned into the HindIII to SmaI sites of pUC119 (described in Vieira and Messing, or. cit.). This clone was named pSVORAA.

b) The EcoRI site at 5716 was removed by partial digestion with EcoRI and filling in with Klenow. The colonies obtained from self-ligation after fill-in were screened and the correct clone was isolated and named pSVORAADRI 11. The deleted EcoRI site was checked by sequencing and shown to be correct.

c) The HpaI (5573) to HindIII (6136) fragment of pSVORAADRI 11 was isolated and inserted into pCMVE/PSP6-L (see 4 above).

6. pCMVEIPSP6-L-SVOrAADRI (step 5) was cut with EcoRI at 9999, blunted and self-ligated. A clone without an EcoRI site was identified and named pRK.

7. pRK was cut with SmaI and BamHI. This was filled in with Klenow and relegated. The colonies were screened. A positive clone was identified and named pRKDBam/Sma3.

8. The HindIII site of pRKDBam/Sma3 was converted to a HeaI site using a converter. (A converter is a piece of DNA used to change one restriction site to another. In this case one end would be complementary to a HindIII sticky end and the other end would have a recognition site for HpaI.) A positive clone was identified and named pRKDBam/Sma, HIII-HpaI 1.

9. pRKDBam/Sma, HIII-HpaI 1 was cut with PstI and NotI and an EcoRI-HindIII linker and HindIII-EcoRI linker were ligated in. Clones for each linker were found. However, it was also determined that too many of the HpaI converters had gone in (two or more converters generate a PvuII site). Therefore, these clones had to be cut with HpaI and self-ligated.

10. RI-HIII clone 3 and HIII-RI clone 5 were cut with HpaI, diluted, and self-ligated. Positives were identified. The RI-HIII clone was named pRK5.

B. Construction of pRK5.veaf.6

The clone I.vegf.6 was treated with EcoRI and the EcoRI insert was isolated and ligated into the vector fragment of pRK5 obtained by digestion of pRK5 with EcoRI and isolation of the large fragment. The two-part ligation of these fragments yielded the expression vector, pRK5.vegf.6, which was screened for the correct orientation of the VEGF-encoding sequence with respect to the promoter.

Further details concerning the construction of the basic pRK5 vector can be taken from U.S. Pat. No. 5,332,671 that issued on Jul. 26, 1994, said patent being expressly incorporated herein by reference.

EXAMPLE 2

The following example details the methodology generally employed to prepare the various VEGF mutants covered by the present invention. The basic expression vector was prepared as follows: Vector SDVF$_{165}$ containing the cDNA of VEGF$_{165}$ was obtained. The cDNA for VEGF$_{165}$ was isolated from SDVF$_{165}$ by restriction digestion with Hind III and Eco RI. This isolated insert was ligated into the pRK5 plasmid taking advantage to the existence therein of Eco RI and Hind III sites. The resultant plasmid was transformed into competent CJ236 *E. coli* cells to make a template for site-directed mutagenesis. The corresponding oligonucleotide containing the mutated site was then prepared—see infra—and the in vitro site-directed mutagenesis step was conducted in accordance with known procedures using the BioRad Muta-Gene mutagenesis kit. After sequencing to determine that the mutagenized site was incorporated into the final expression vector, the resultant vector was transfected into 293 human kidney cells for transient expression.

The following oligonucleotides were prepared in order to make the final mutated product.

TABLE 2

| Mutation | 5' to 3' Sequence | |
|---|---|---|
| C51D | CAGGGGCACATCGGATGGCTTGAA | (SEQ ID NO:7) |
| C51A | CAGGGGCACGGCGGATGGCTTGAA | (SEQ ID NO:8) |
| C60D | GTCATTGCAATCGCCCCCGCATCG | (SEQ ID NO:9) |
| C60A | GTCATTGCAGGCGCCCCCGCATCG | (SEQ ID NO:10) |
| C51A, C60A | GTCATTGCAGGCGCCCCCGCATCGCATCAGG GGCACGGCGGATGGCTTGAA | (SEQ ID NO:11) |
| C51D, C60D | GTCATTGCAATCGCCCCCGCATCGCATCAGGG GCACATCGGATGGCTTGAA | (SEQ ID NO:12) |

Thus prepared in accordance with the insertion of the oligonucleotides set forth in Table 2 above, left column there are prepared at the corresponding mutation in the VEGF molecule in accordance with the notation given under the left hand column entitled "Mutation". The naming of the compound is in accord with naming convention. Thus, for the first entry the mutation is referred to as "C51D". This means that at the 51 amino acid position of the VEGF molecule the cysteine (C) residue was mutated so as to insert an aspartic acid (D) at that 51 position.

FIG. 2 is a diagram showing the native VEGF dimer and certain of the variant VEGF polypeptides of the present invention. As shown in FIG. 2, the native VEGF molecule dimerizes through the formation of disulfide bonds between the cysteine at amino acid position 51 on one monomer and the cysteine at amino acid position 60 on the other monomer and vice versa. Changing the cysteine residue at amino acid position 51 or 60 to aspartic acid (C51D or C60D, respectively) prevents proper dimerization and the formation of staggered dimer molecules. Changing both cysteine residues at amino acid positions 51 and 60 (C51D, C60D) prevents dimer formation altogether. Binding of VEGF Varants to VEGF Receptors—Native VEGF dimer and the VEGF variant polypeptides shown in FIG. 2 were tested for the ability to bind to the KDR and FLT-1 receptors. Receptor binding assays were performed as described above. The results obtained for binding to the KDR receptor are presented in FIGS. 3 and 4.

Figure 3:
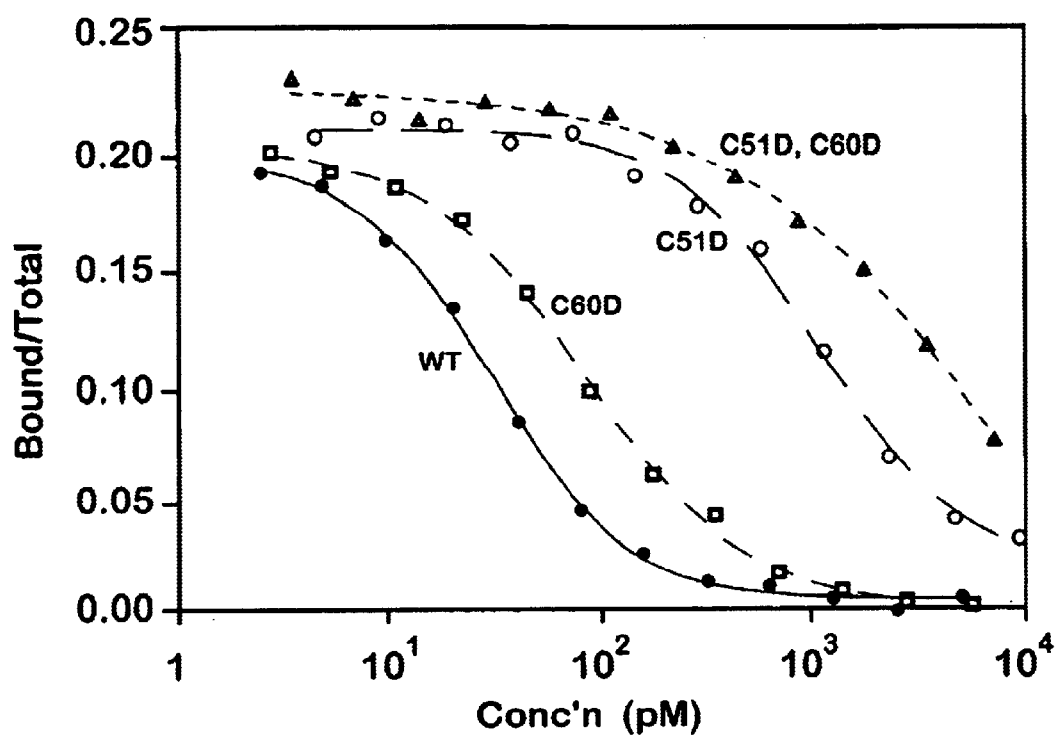
FIG. 3 is a graph showing the binding profiles of native VEGF dimer ("•"), the staggered dimer formed from the C60D variant VEGF polypeptide ("□"), the staggered dimer formed from the C51D variant VEGF polypeptide ("○") and the monomeric VEGF variant polypeptide C51D, C60D ("Δ") to the KDR receptor. Data is presented as the ratio of bound polypeptide to free versus the picomolar (pM) concentration of unlabeled competitor.
Figure 4:
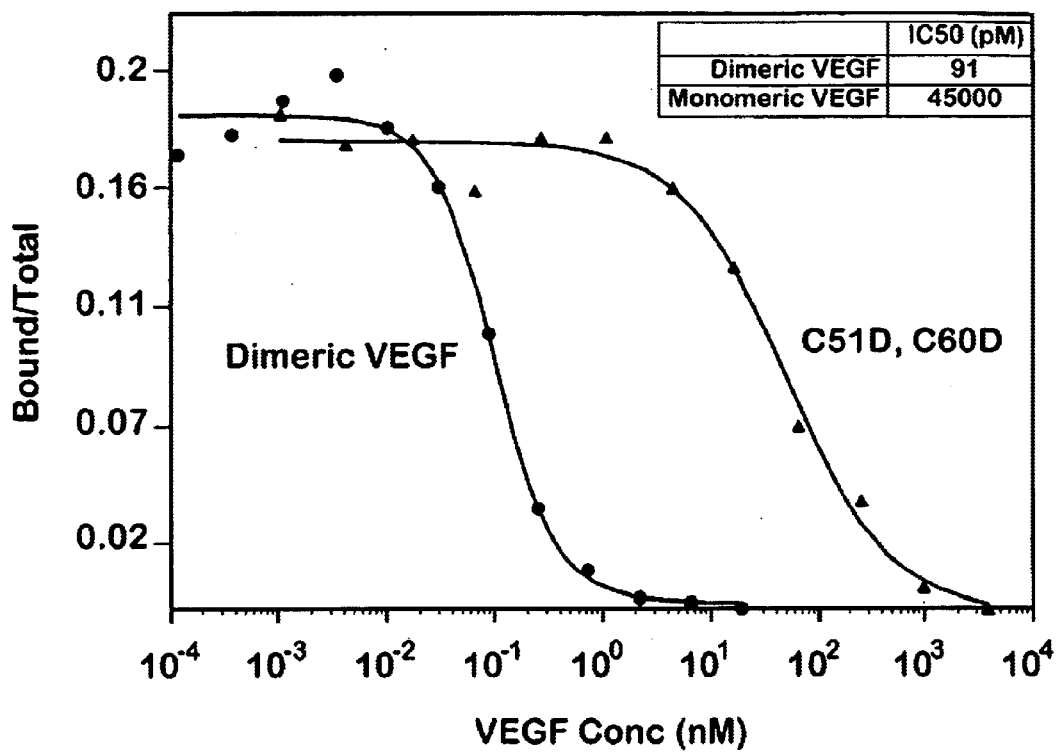
FIG. 4 is a graph showing the binding profiles of native VEGF dimer ("•"), and the monomeric VEGF variant polypeptide C51D, C60D ("▲") to the KDR receptor. Data is presented as the ratio of bound polypeptide to free versus the nanomolar (nM) concentration of unlabeled VEGF competitor.

As shown in FIG. 3, all of the three VEGF variant polypeptides tested retained the ability to bind to the KDR receptor, although none exhibited a binding affinity as great as the native VEGF dimer protein. The results presented in FIG. 3 also demonstrate that the monomeric variant polypeptide C51D, C60D retains the ability to bind to the KDR receptor, however, it does so with a reduced binding affinity as compared to the native dimer or two staggered dimers tested. FIG. 4 demonstrates that the binding affinity of the C51D, C60D monomeric variant for the KDR receptor is approximately 500-fold less than the native dimeric VEGF protein. Thus, these results demonstrate that each of the VEGF variant polypeptides tested retain the ability to bind to the KDR receptor, although at a lower binding affinity.

Figure 5:
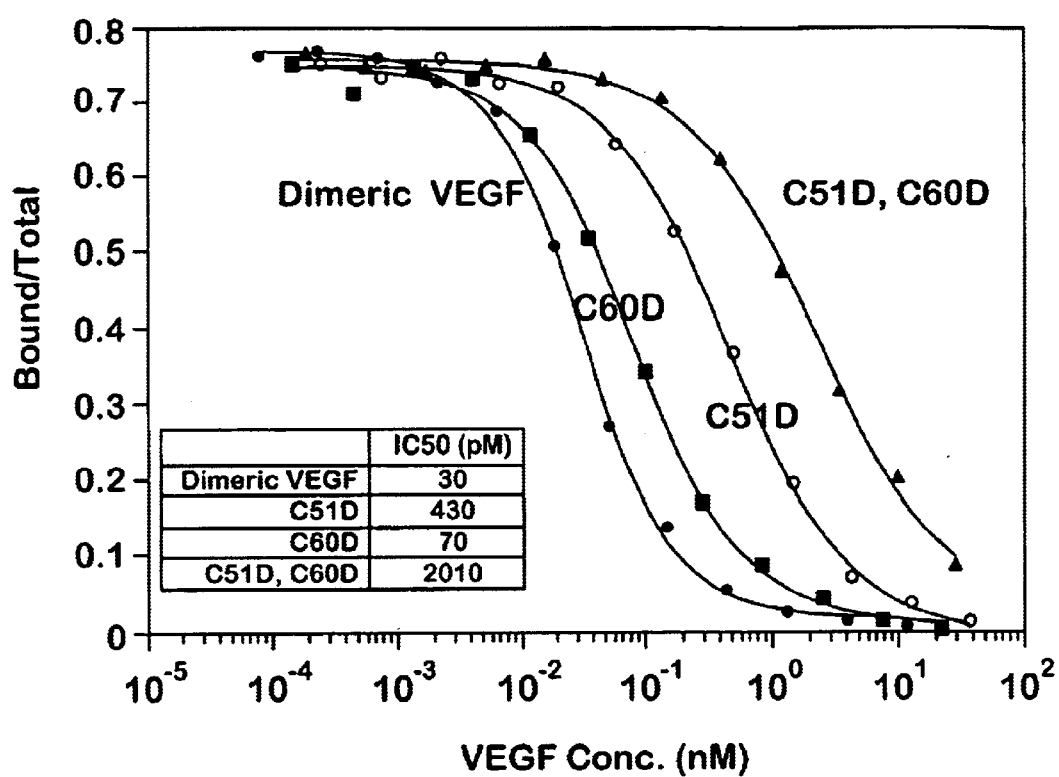
FIG. 5 is a graph showing the binding profiles of native VEGF dimer ("•"), the staggered dimer formed from the C60D variant VEGF polypeptide ("■"), the staggered dimer formed from the C51D variant VEGF polypeptide ("○") and the monomeric VEGF variant polypeptide C51D, C60D ("▲") to the FLT-1 receptor. Data is presented as the ratio of bound polypeptide to free versus the nanomolar (nM) concentration of unlabeled VEGF competitor.
Figure 6:
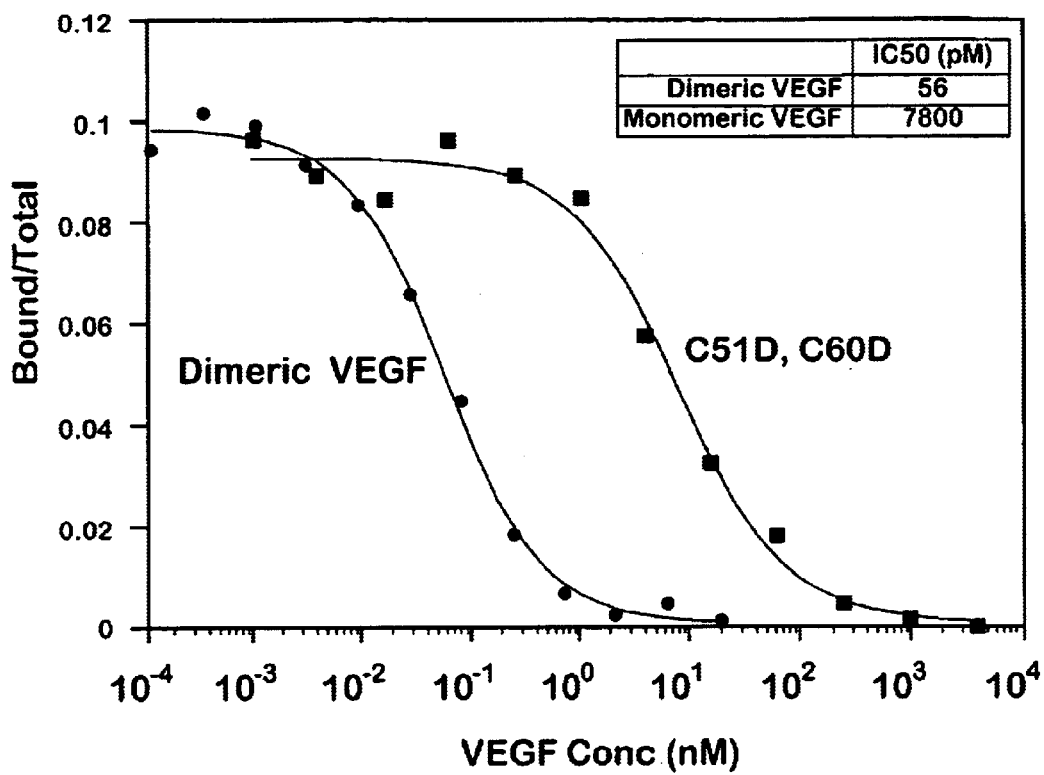
FIG. 6 is a graph showing the binding profiles of native VEGF dimer ("•") and the monomeric VEGF variant polypeptide C51D, C60D ("■") to the FLT-1 receptor. Data is presented as the ratio of bound polypeptide to free versus the nanomolar (nM) concentration of unlabeled VEGF competitor.

FIGS. 5 and 6 show the results obtained when measuring the binding of the polypeptides of FIG. 2 to the FLT-1 receptor. The results presented in FIG. 5 demonstrate that all of the variants tested retain the ability to bind to the FLT-1 receptor, although at reduced binding affinities as compared to the native VEGF dimer. FIG. 6 demonstrates that the binding affinity of the C51D, C60D monomeric variant is approximately 140-less for the FLT-1 receptor than exhibited by the native VEGF dimer. Thus, these results demonstrate that each of the VEGF variant polypeptides tested retain the ability to bind to the FLT-1 receptor, although at a lower binding affinity.

Stimulation of Mitogenesis by VEGF and Variants Thereof—Because the VEGF variants shown in FIG. 2 were shown above to be capable of binding to both the KDR and FLT-1 receptors, these variants were also tested for their ability to stimulate mitogenesis in endothelial cells. The mitogenic stimulation assays were performed as described above. The results from these assays are presented in FIG. 7.

Figure 7:
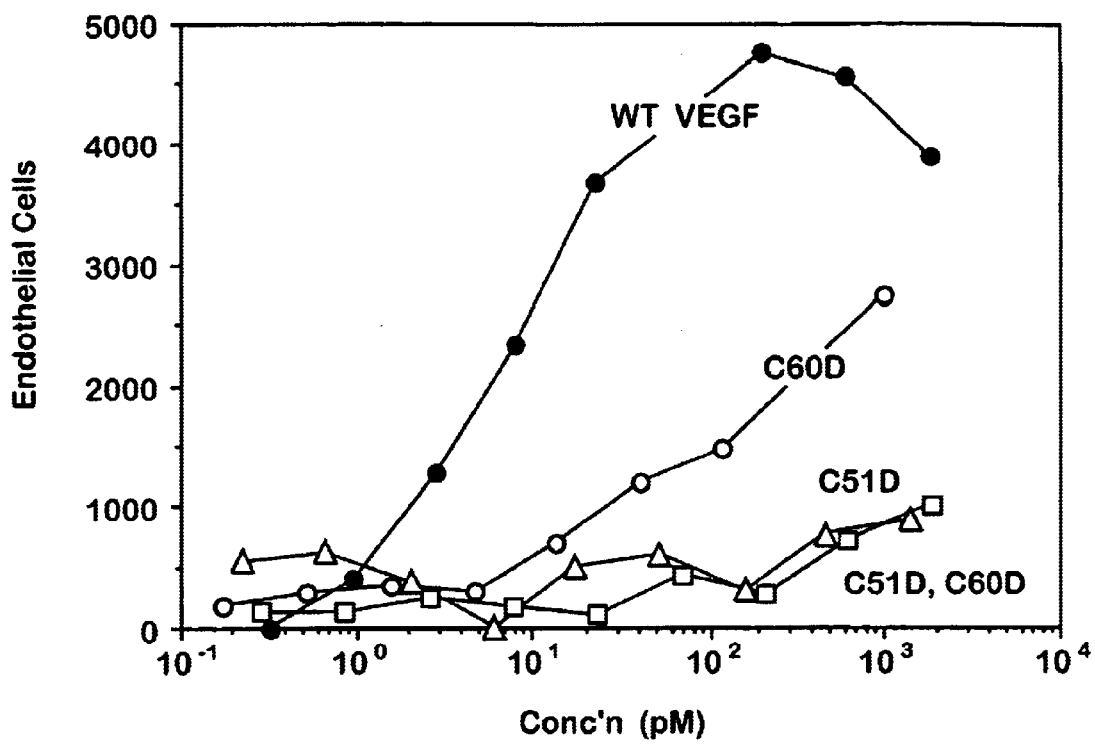
FIG. 7 is a graph demonstrating the ability of the native VEGF dimer ("•"), the staggered dimer formed from the C60D variant VEGF polypeptide ("○"), the staggered dimer formed from the C51D variant VEGF polypeptide ("Δ") and the monomeric VEGF variant polypeptide C51D, C60D ("□") to stimulate mitogenesis in endothelial cells. Data is presented as the total number of endothelial cells versus the picomolar (pM) concentration of polypeptide employed.

As is shown in FIG. 7, while the native VEGF dimer molecule is capable of efficiently stimulating mitogenesis in endothelial cells, the VEGF variants tested (staggered dimers C51D and C60D as well as the monomeric variant C51D, C60D) exhibit an inhibitory effect on the mitogenic stimulation of endothelial cells. These results demonstrate that proper dimerization between the cysteine residues at amino acid positions 51 and 60 of the native VEGF polypeptide is essential for efficient mitogenic stimulation of endothelial cells. As such, these data demonstrate that amino acid modifications which disrupt the ability of VEGF monomeric units to properly dimerize function to inhibit the mitogenic activity of the molecule. Given that these variant molecule are capable of binding to and occupying the VEGF receptors without inducing a "native-VEGF-like" mitogenic response, such variant molecules may serve as effective antagonists of VEGF activity.

Ability of the C51D, C60D Monomer to Inhibit VEGF-induced Endothelial Cell Growth—The C51D, C60D monomer polypeptide was employed in assays designed to measure the ability of the monomer to inhibit the VEGF-induced growth of endothelial cells. Briefly, endothelial cells were cultured in the presence of 3 ng/ml VEGF and varying amounts of either the A461 anti-VEGF monoclonal antibody or the C51D, C60D monomer polypeptide. The results demonstrating the inhibitory effects of each inhibitor on endothelial cell growth are presented in FIG. 8.

Figure 8:
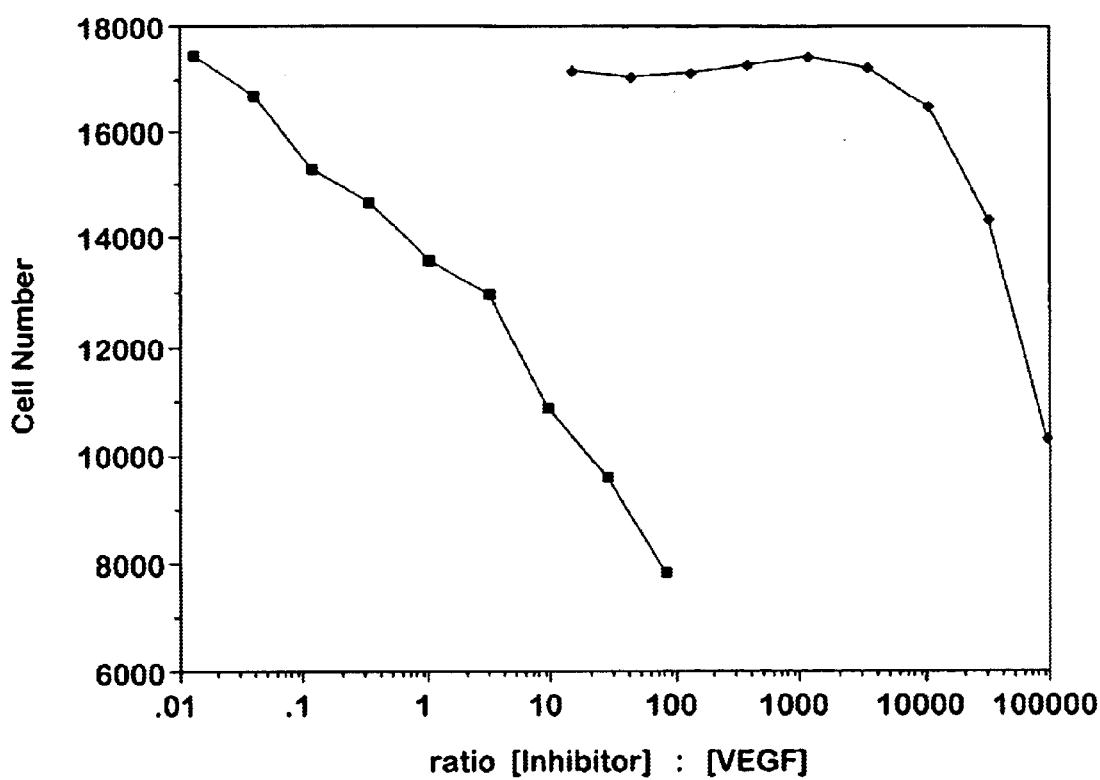
FIG. 8 is a graph demonstrating the ability of the anti-VEGF monoclonal antibody A461 ("■") and the monomeric VEGF variant polypeptide C51D, C60D ("•") to inhibit VEGF-induced growth of endothelial cells. Data is presented as the total number of endothelial cells versus the ratio of antibody or monomer inhibitor to VEGF employed.

The results presented in FIG. 8 demonstrate that both the A461 anti-VEGF monoclonal antibody and the C51D, C60D monomer polypeptide exhibit substantial inhibitory effects on VEGF-induced endothelial cell growth. These inhibitory effects increase as the ratio of inhibitor to VEGF increases. As such, the C51D, C60D monomer polypeptide functions to inhibit the endothelial growth activating effect of VEGF.

Concluding Remarks

The foregoing description details specific methods which can be employed to practice the present invention. Having detailed such specific methods, those skilled in the art will well enough know how to devise alternative reliable methods at arriving at the same information in using the fruits of the present invention. Thus, however detailed the foregoing may appear in text, it should not be construed as limiting the overall scope thereof; rather, the ambit of the present invention is to be determined only by the lawful construction of the appended claims. All documents cited herein are hereby expressly incorporated by reference.

What is claimed is:

1. A variant vascular endothelial cell growth factor (VEGF) polypeptide which is capable of binding to a VEGF receptor without significantly inducing a VEGF response, said variant polypeptide comprising an amino acid modification of at least one cysteine residue at positions 51 and/or 60 of the native VEGF amino acid sequence, wherein said amino acid modification inhibits dimulfide bond formation.

2. The variant VEGF polypeptide according to claim 1 wherein said amino acid modification is a substitution of said at least on cysteine residue with a different amino acid which is incapable of participating in the formation of a disulfide bond.

3. The variant VEGF polypeptide according to claim 1 wherein said VEGF polypeptide is capable of inhibiting induction of a VEGF response.

4. The variant VEGF polypeptide according to claim 3 wherein said VEGF response is mitogenic activity.

5. The variant VEGF polypeptide according to claim 2 wherein two cysteine are substituted with a different amino acid at amino acid positions 51 and 60.

6. The variant VEGA polypeptide according to claim 2 wherein said cysteine is at amino acid position 51.

7. The variant VEGF polypeptide according to claim 2 wherein said cysteine is at amino acid position 60.

8. The variant VEGF polypeptide according to claim 2 wherein aspartic acid is substituted for cysteine.

9. The variant VEGF polypeptide according to claim 6 comprising the substitution C51D.

10. The variant VEGF polypeptide according to claim 7 comprising the substitution C60D.

11. The variant VEGF polypeptide according to claim 1 wherein said amino acid modification is a chemical modification of said at least one cysteine residue which renders said cysteine residue incapable of participating in the formation of a disulfide bond.

12. An isolated nucleic acid sequence comprising a sequence that encodes the variant VEGF polypeptide of claim 1.

13. A replicable expression vector capable in a transformant host cell of expressing the nucleic acid of claim 12.

14. Host cells transformed with the vector according to claim 13.

15. Host cells according to claim 14 which are Chinese hamster ovary cells.

16. A composition of matter comprising the variant VEGF polypeptide according to claim 1 in combination with a pharmaceutically acceptable carrier.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:1:

CCTATGGCTG AAGGCGGCCA GAAGCCTCAC GAAGTGGTGA AGTTCATGGA CGTGTATCA        59

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:2:

AGTAGCAAGC TTGACGTGTG GCAGGCTTGA                                        30

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:3:

GATCTGGCCA TACACTTGAG TGACAATGA                                         29

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:4:

CATCCACTTT GCCTTTCTCT CCACAGGT                                          28

(2) INFORMATION FOR SEQ ID NO:5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:5:

GTCCACTCCC AG                                                                12

(2) INFORMATION FOR SEQ ID NO:6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:6:

AGGCTGCTGC AGTTCGACGT GGGAGTGGAC                                             30

(2) INFORMATION FOR SEQ ID NO:7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:7:

CAGGGGCACA TCGGATGGCT TGAA                                                   24

(2) INFORMATION FOR SEQ ID NO:8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:8:

CAGGGGCACG GCGGATGGCT TGAA                                                   24

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:9:

GTCATTGCAA TCGCCCCCGC ATCG                                                   24

(2) INFORMATION FOR SEQ ID NO:10:

(i) SEQUENCE CHARACTERISTICS:
            (A) LENGTH: 24 base pairs
            (B) TYPE: nucleic acid
            (C) STRANDEDNESS: single (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:10:

GTCATTGCAG GCGCCCCCGC ATCG                                              24

(2) INFORMATION FOR SEQ ID NO:11:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:11:

GTCATTGCAG GCGCCCCCGC ATCGCATCAG GGGCACGGCG GATGGCTTGA A                 51

(2) INFORMATION FOR SEQ ID NO:12:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:12:

GTCATTGCAA TCGCCCCCGC ATCGCATCAG GGGCACATCG GATGGCTTGA A                 51

(2) INFORMATION FOR SEQ ID NO:13:

(i) SEQUENCE CHARACTERISTICS:
        (A) LENGTH: 990 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 57..633

(xi) SEQUENCE DESCRIPTION: SEQ ID NO:13:

CAGTGTGCTG GCGGCCCGGC GCGAGCCGGC CCGGCCCCGG TCGGGCCTCC GAAACC            56

ATG AAC TTT CTG CTG TCT TGG GTG CAT TGG AGC CTC GCC TTG CTG CTC         104
Met Asn Phe Leu Leu Ser Trp Val His Trp Ser Leu Ala Leu Leu Leu
 1               5                  10                  15

TAC CTC CAC CAT GCC AAG TGG TCC CAG GCT GCA CCC ATG GCA GAA GGA         152
Tyr Leu His His Ala Lys Trp Ser Gln Ala Ala Pro Met Ala Glu Gly
                 20                  25                  30

GGA GGG CAG AAT CAT CAC GAA GTG GTG AAG TTC ATG GAT GTC TAT CAG         200
Gly Gly Gln Asn His His Glu Val Val Lys Phe Met Asp Val Tyr Gln
             35                  40                  45

CGC AGC TAC TGC CAT CCA ATC GAG ACC CTG GTG GAC ATC TTC CAG GAG         248
Arg Ser Tyr Cys His Pro Ile Glu Thr Leu Val Asp Ile Phe Gln Glu
         50                  55                  60

TAC CCT GAT GAG ATC GAG TAC ATC TTC AAG CCA TCC TGT GTG CCC CTG         296
Tyr Pro Asp Glu Ile Glu Tyr Ile Phe Lys Pro Ser Cys Val Pro Leu
 65                  70                  75                  80

```
ATG CGA TGC GGG GGC TGC TGC AAT GAC GAG GGC CTG GAG TGT GTG CCC       344
Met Arg Cys Gly Gly Cys Cys Asn Asp Glu Gly Leu Glu Cys Val Pro
                85                  90                  95

ACT GAG GAG TCC AAC ATC ACC ATG CAG ATT ATG CGG ATC AAA CCT CAC       392
Thr Glu Glu Ser Asn Ile Thr Met Gln Ile Met Arg Ile Lys Pro His
                100                 105                 110

CAA GGC CAG CAC ATA GGA GAG ATG AGC TTC CTA CAG CAC AAC AAA TGT       440
Gln Gly Gln His Ile Gly Glu Met Ser Phe Leu Gln His Asn Lys Cys
                115                 120                 125

GAA TGC AGA CCA AAG AAA GAT AGA GCA AGA CAA GAA AAT CCC TGT GGG       488
Glu Cys Arg Pro Lys Lys Asp Arg Ala Arg Gln Glu Asn Pro Cys Gly
        130                 135                 140

CCT TGC TCA GAG CGG AGA AAG CAT TTG TTT GTA CAA GAT CCG CAG ACG       536
Pro Cys Ser Glu Arg Arg Lys His Leu Phe Val Gln Asp Pro Gln Thr
145                 150                 155                 160

TGT AAA TGT TCC TGC AAA AAC ACA GAC TCG CGT TGC AAG GCG AGG CAG       584
Cys Lys Cys Ser Cys Lys Asn Thr Asp Ser Arg Cys Lys Ala Arg Gln
                165                 170                 175

CTT GAG TTA AAC GAA CGT ACT TGC AGA TGT GAC AAG CCC AGG CGG TGA G    633
Leu Glu Leu Asn Glu Arg Thr Cys Arg Cys Asp Lys Pro Arg Arg   *
                180                 185                 190

CCGGGCAGGA GGAAGGAGCC TCCCTCAGGG TTTCGGGAAC CAGATCTCTC ACCAGGAAAG     693

ACTGATACAG AACGATCGAT ACAGAAACCA CGCTGCCGCC ACCACACCAT CACCATCGAC     753

AGAACAGTCC TTAATCCAGA AACCTGAAAT GAAGGAAGAG GAGACTCTGC GCAGAGCACT     813

TTGGGTCCGG AGGGCGAGAC TCCGGCGGAA GCATTCCCGG GCGGGTGACC CAGCACGGTC     873

CCTCTTGGAA TTGGATTCGC CATTTTATTT TTCTTGCTGC TAAATCACCG AGCCCGGAAG     933

ATTAGAGAGT TTTATTTCTG GGATTCCTGT AGACACACCG CGGCCGCCAG CACACTG        990

(2) INFORMATION FOR SEQ ID NO:14:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO:14:

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
        130                 135                 140
```

—continued

```
Pro Cys Ser Glu Arg Arg Lys His Leu Phe Val Gln Asp Pro Gln Thr
145             150                 155             160

Cys Lys Cys Ser Cys Lys Asn Thr Asp Ser Arg Cys Lys Ala Arg Gln
            165                 170             175

Leu Glu Leu Asn Glu Arg Thr Cys Arg Cys Asp Lys Pro Arg Arg
            180             185             190
```